US005948629A

United States Patent [19]
Fasano

[11] Patent Number: 5,948,629
[45] Date of Patent: Sep. 7, 1999

[54] ZONULA OCCLUDENS TOXIC RECEPTOR

[75] Inventor: Alessio Fasano, Ellicott City, Md.

[73] Assignee: University of Maryland at Baltimore, Baltimore, Md.

[21] Appl. No.: 09/186,409

[22] Filed: Nov. 5, 1998

Related U.S. Application Data

[60] Division of application No. 09/024,198, Feb. 17, 1998, which is a continuation-in-part of application No. 08/803,364, Feb. 20, 1997, Pat. No. 5,864,014.

[51] Int. Cl.⁶ .......................... G01N 33/53; C07K 14/705
[52] U.S. Cl. .......................... 435/7.32; 435/909; 435/7.8; 435/7.91; 435/7.9; 435/7.92; 435/7.93; 435/7.94; 435/7.95; 435/7.22; 435/7.1; 530/350; 530/326; 530/412; 530/413; 530/825; 530/300
[58] Field of Search .............................. 435/7.1, 909, 7.8, 435/7.91, 7.9, 7.92, 7.93, 7.94, 7.95, 7.32, 7.22; 530/350, 326, 412, 413, 825, 300

[56] References Cited

U.S. PATENT DOCUMENTS 5,665,389 9/1997 Fasano .

FOREIGN PATENT DOCUMENTS

WO 96/37196 11/1996 WIPO .

OTHER PUBLICATIONS

Fasano et al, *Gastroenterology*, 112:839–846 (1997).
Goding et al, In: *Monoclonal Antibodies: Principles and Practice*, pp. 219–240, London, Academic Press 1986.
Fiore et al, *Gastroenterology*, 110:A323 (1996).
Fasano et al, *The Journal of Clinical Investigations, Inc.*, 96:710–720 (1995).
Hall et al, *J. Med. Biol.*, 211:11–16 (1990).
Dong et al, *Eur. J. Biochem.*, 227:636–646 (1994).
Ridley et al, *Cell*, 70:389–399 (1992).
Cautrecases et al, *Method in Enzymology*, XXII:345–355 and 373–377 (1971).
Philp, *The Protein Protocols Handbook*, pp. 393–398, Ed. John M. Walker 1996, Humana Press, Totowa, New Jersey.
Hass et al, *J. Biol. Chem.*, 265(12):6921–6927 (1990).

*Primary Examiner*—Anthony C. Caputa
*Assistant Examiner*—Khalid Masood
*Attorney, Agent, or Firm*—Sughrue, Mion, Zinn, Macpeak & Seas, PLLC

[57] ABSTRACT

Receptors for the zonula occludens toxin of *Vibrio cholera*, as well as methods involving the use of the same are disclosed.

2 Claims, 4 Drawing Sheets

FIG. 1
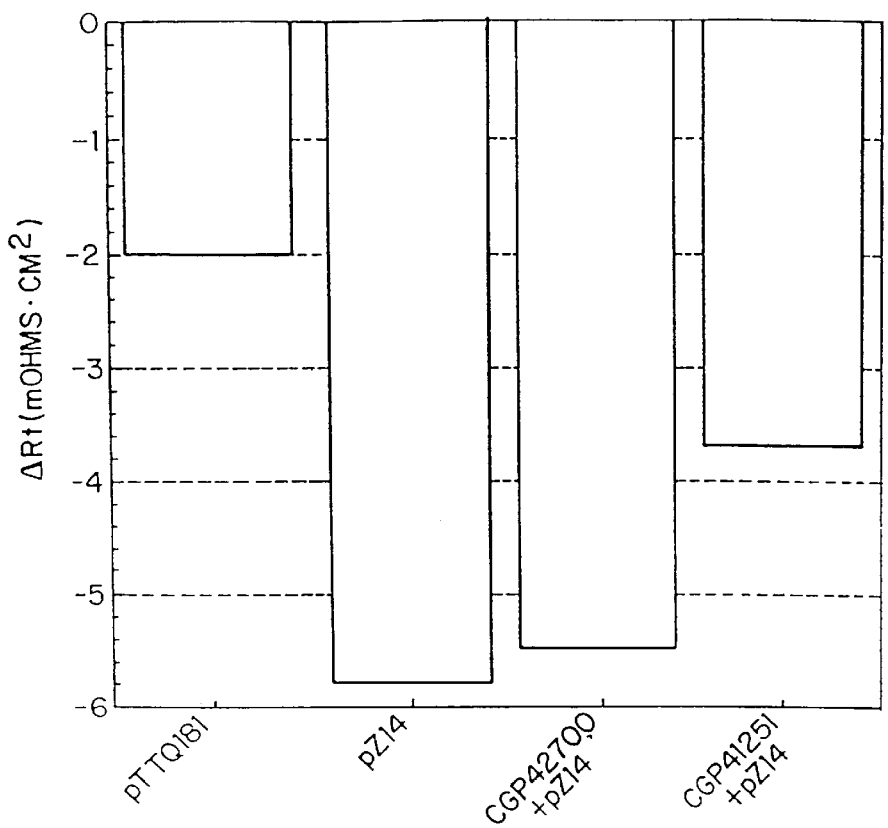
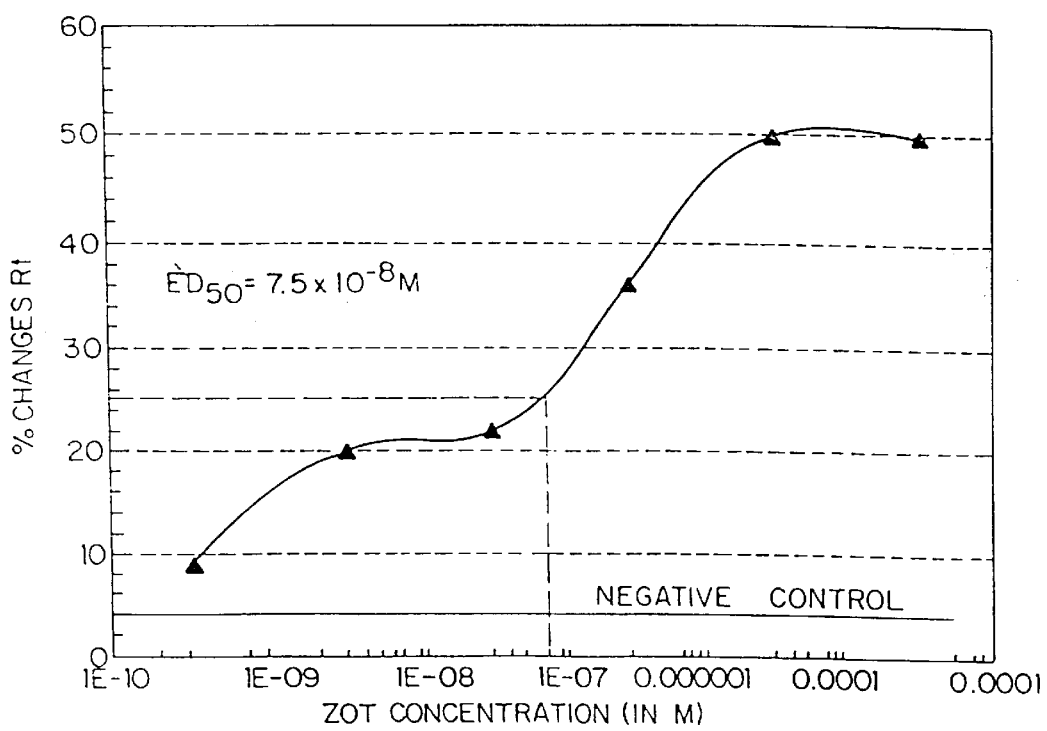
FIG. 3

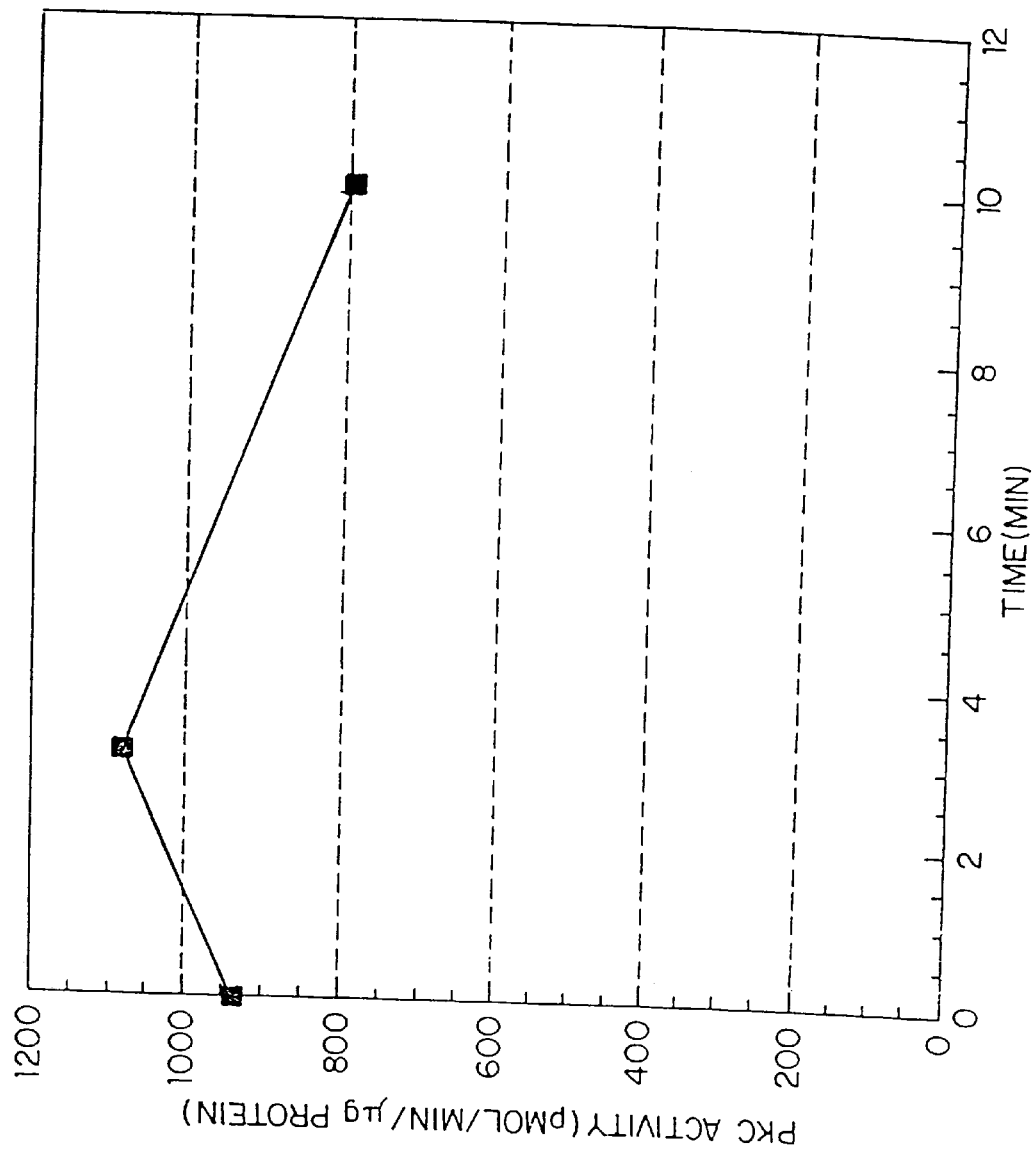

ZONULA OCCLUDENS TOXIC RECEPTOR

CROSS-REFERENCE TO RELATED APPLICATIONS

This is a Divisional of U.S. application Ser. No. 09/024,198, filed Feb. 17, 1998; which in turn is a Continuation-in-Part of U.S. application Ser. No. 08/803,364, U.S. Pat. No. 5,864,014 filed Feb. 20, 1997.

The invention was supported by the University of Maryland, Baltimore, Md. The invention described herein was supported by funding from the National Institutes of Health (NIH AI35740; NIH DK 48373 and NIH AI19716). The Government has certain rights.

FIELD OF THE INVENTION

The present invention relates to receptors for the zonula occludens toxin of *Vibrio cholera*, as well as methods involving the use of the same.

BACKGROUND OF THE INVENTION

I. Function and Regulation of Intestinal Tight Junctions

The tight junctions (hereinafter "tj") or zonula occludens (hereinafter "ZO") are one of the hallmarks of absorptive and secretory epithelia (Madara, *J. Clin. Invest.*, 83:1089–1094 (1989); and Madara, *Textbook of Secretory Diarrhea Eds.* Lebenthal et al, Chapter 11, pages 125–138 (1990)). As a barrier between apical and basolateral compartments, they selectively regulate the passive diffusion of ions and water-soluble solutes through the paracellular pathway (Gumbiner, *Am. J. Physiol.*, 253 (*Cell Physiol.* 22):C749–C758 (1987)). This barrier maintains any gradient generated by the activity of pathways associated with the transcellular route (Diamond, *Physiologist*, 20:10–18 (1977)).

Variations in transepithelial conductance can usually be attributed to changes in the permeability of the paracellular pathway, since the resistances of enterocyte plasma membranes are relatively high (Madara, supra). The ZO represents the major barrier in this paracellular pathway, and the electrical resistance of epithelial tissues seems to depend on the number of transmembrane protein strands, and their complexity in the ZO, as observed by freeze-fracture electron microscopy (Madara et al, *J. Cell Biol.*, 101:2124–2133 (1985)).

There is abundant evidence that ZO, once regarded as static structures, are in fact dynamic and readily adapt to a variety of developmental (Magnuson et al, *Dev. Biol.*, 67:214–224 (1978); Revel et al, *Cold Spring Harbor Symp. Quant. Biol.*, 40:443–455 (1976); and Schneeberger et al, *J. Cell Sci.*, 32:307–324 (1978)), physiological (Gilula et al, *Dev. Biol.*, 50:142–168 (1976); Madara et al, *J. Membr. Biol.*, 100:149–164 (1987); Mazariegos et al, *J. Cell Biol.*, 98:1865–1877 (1984); and Sardet et al, *J. Cell Biol.*, 80:96–117 (1979)), and pathological (Milks et al, *J. Cell Biol.*, 103:2729–2738 (1986); Nash et al, *Lab. Invest.*, 59:531–537 (1988); and Shasby et al, *Am. J. Physiol.*, 255(*Cell Physiol.*, 24):C781–C788 (1988)) circumstances. The regulatory mechanisms that underlie this adaptation are still not completely understood. However, it is clear that, in the presence of $Ca^{2+}$, assembly of the ZO is the result of cellular interactions that trigger a complex cascade of biochemical events that ultimately lead to the formation and modulation of an organized network of ZO elements, the composition of which has been only partially characterized (Diamond, *Physiologist*, 20:10–18 (1977)). A candidate for the transmembrane protein strands, occludin, has recently been identified (Furuse et al, *J. Membr. Biol.*, 87:141–150 (1985)).

Six proteins have been identified in a cytoplasmic submembranous plaque underlying membrane contacts, but their function remains to be established (Diamond, supra). ZO-1 and ZO-2 exist as a heterodimer (Gumbiner et al, *Proc. Natl. Acad. Sci., USA*, 88:3460–3464 (1991)) in a detergent-stable complex with an uncharacterized 130 kD protein (ZO-3). Most immunoelectron microscopic studies have localized ZO-1 to precisely beneath membrane contacts (Stevenson et al, *Molec. Cell Biochem.*, 83:129–145 (1988)). Two other proteins, cingulin (Citi et al, Nature (London), 333:272–275 (1988)) and the 7H6 antigen (Zhong et al, *J. Cell Biol.*, 120:477–483 (1993)) are localized further from the membrane, and have not yet been cloned. Rab 13, a small GTP binding protein has also recently been localized to the junction region (Zahraoui et al, *J. Cell Biol.*, 124:101–115 (1994)). Other small GTP-binding proteins are known to regulate the cortical cytoskeleton, i.e., rho, regulates actin-membrane attachment in focal contacts (Ridley et al, *Cell*, 70:389–399 (1992)), and rac, regulates growth factor-induced membrane ruffling (Ridley et al, *Cell*, 70:401–410 (1992)). Based on the analogy with the known functions of plaque proteins in the better characterized cell junctions, focal contacts (Guan et al, *Nature*, 358:690–692 (1992)), and adherens junctions (Tsukita et al, *J. Cell Biol.*, 123:1049–1053 (1993)), it has been hypothesized that tj-associated plaque proteins are involved in transducing signals in both directions across the cell membrane, and in regulating links to the cortical actin cytoskeleton.

To meet the many diverse physiological and pathological challenges to which epithelia are subjected, the ZO must be capable of rapid and coordinated responses that require the presence of a complex regulatory system. The precise characterization of the mechanisms involved in the assembly and regulation of the ZO is an area of current active investigation.

There is now a body of evidence that tj structural and functional linkages exist between the actin cytoskeleton and the tj complex of absorptive cells (Gumbiner et al, supra; Madara et al, supra; and Drenchahn et al, *J. Cell Biol.*, 107:1037–1048 (1988)). The actin cytoskeleton is composed of a complicated meshwork of microfilaments whose precise geometry is regulated by a large cadre of actin-binding proteins. An example of how the state of phosphorylation of an actin-binding protein might regulate cytoskeletal linking to the cell plasma membrane is the myristoylated alanine-rich C kinase substrate (hereinafter "MARCKS"). MARCKS is a specific protein kinase C (hereinafter "PKC") substrate that is associated with the cytoplasmic face of the plasma membrane (Aderem, *Elsevier Sci. Pub.* (UK), pages 438–443 (1992)). In its non-phosphorylated form, MARCKS crosslinks to the membrane actin. Thus, it is likely that the actin meshwork associated with the membrane via MARCKS is relatively rigid (Hartwig et al, *Nature*, 356:618–622 (1992)). Activated PKC phosphorylates MARCKS, which is released from the membrane (Rosen et al, *J. Exp. Med.*, 172:1211–1215 (1990); and Thelen et al, *Nature*, 351:320–322 (1991)). The actin linked to MARCKS is likely to be spatially separated from the membrane and be more plastic. When MARCKS is dephosphorylated, it returns to the membrane where it once again crosslinks actin (Hartwig et al, supra; and Thelen et al, supra). These data suggest that the F-actin network may be rearranged by a PKC-dependent phosphorylation process that involves actin-binding proteins (MARCKS being one of them).

A variety of intracellular mediators have been shown to alter tj function and/or structure. Tight junctions of amphibian gallbladder (Duffey et al, *Nature*, 204:451–452 (1981)), and both goldfish (Bakker et al, *Am. J. Physiol.*, 246:G213–G217 (1984)) and flounder (Krasney et al, *Fed. Proc.*, 42:1100 (1983)) intestine, display enhanced resistance to passive ion flow as intracellular cAMP is elevated. Also, exposure of amphibian gallbladder to $Ca^{2+}$ ionophore appears to enhance tj resistance, and induce alterations in tj structure (Palant et al, *Am. J. Physiol.*, 245:C203–C212 (1983)). Further, activation of PKC by phorbol esters increases paracellular permeability both in kidney (Ellis et al, *C. Am. J. Physiol.*, 263 (*Renal Fluid Electrolyte Physiol.* 32:F293–F300 (1992)), and intestinal (Stenson et al, *C. Am. J. Physiol.*, 265 (*Gastrointest. Liver Physiol.*, 28):G955–G962 (1993)) epithelial cell lines.

II. Zonula Occludens Toxin

Most *Vibrio cholerae* vaccine candidates constructed by deleting the ctxA gene encoding cholera toxin (CT) are able to elicit high antibody responses, but more than one-half of the vaccinees still develop mild diarrhea (Levine et al, *Infect. Immun.*, 56(1):161–167 (1988)). Given the magnitude of the diarrhea induced in the absence of CT, it was hypothesized that *V. cholerae* produce other enterotoxigenic factors, which are still present in strains deleted of the ctxA sequence (Levine et al, supra). As a result, a second toxin, zonula occludens toxin (hereinafter "ZOT") elaborated by *V. cholerae*, and which contribute to the residual diarrhea, was discovered (Fasano et al, *Proc. Nat. Acad. Sci., USA*, 8:5242–5246 (1991)). The zot gene is located immediately adjacent to the ctx genes. The high percent concurrence of the zot gene with the ctx genes among *V. cholerae* strains (Johnson et al, *J. Clin. Microb.*, 31/3:732–733 (1993); and Karasawa et al, *FEBS Microbiology Letters*, 106:143–146 (1993)) suggests a possible synergistic role of ZOT in the causation of acute dehydrating diarrhea typical of cholera. Recently, the zot gene has also been identified in other enteric pathogens (Tschape, *2nd Asian-Pacific Symposium on Typhoid fever and other Salomellosis*, 47(Abstr.) (1994)).

It has been previously found that, when tested on rabbit ileal mucosa, ZOT increases the intestinal permeability by modulating the structure of intercellular tj (Fasano et al, supra). It has been found that as a consequence of modification of the paracellular pathway, the intestinal mucosa becomes more permeable. It also was found that ZOT does not affect $Na^+$-glucose coupled active transport, is not cytotoxic, and fails to completely abolish the transepithelial resistance (Fasano et al, supra).

More recently, it has been found that ZOT is capable of reversibly opening tj in the intestinal mucosa, and thus ZOT, when co-administered with a therapeutic agent, is able to effect intestinal delivery of the therapeutic agent, when employed in an oral dosage composition for intestinal drug delivery (WO 96/37196; U.S. patent application Ser. No. 08/443,864, (U.S. Pat. No. 5,827,534) filed May 24, 1995; and U.S. patent application Ser. No. 08/598,852, filed Feb. 9, 1996 (now U.S. Pat. No. 5,665,389); each of which is incorporated by reference herein in their entirety). It has also been found that ZOT is capable of reversibly opening tj in the nasal mucosa, and thus ZOT, when co-administered with a therapeutic agent, is able to enhance nasal absorption of a therapeutic agent (U.S. patent application Ser. No. 08/781,057, filed Jan. 9, 1997; which is incorporated by reference herein in its entirety).

In U.S. patent application Ser. No. 08/803,364, (U.S. Pat. No. 5,864,014) filed Feb. 20, 1997; which is incorporated by reference herein in its entirety, a ZOT receptor from CaCo2 cells has been identified and purified. The ZOT receptor represents the first step of a pathway involved in the regulation of epithelial permeability.

In the present invention, the ZOT receptors from heart, intestinal and brain tissue has been identified and isolated.

SUMMARY OF THE INVENTION

An object of the present invention is to identify the ZOT receptor from heart, intestinal and brain tissue.

Another object of the present invention is to use the ZOT receptors in a method for screening for ZOT analogs (antagonist or agonist).

Yet another object of the present invention is to provide ZOT analogs obtainable by said method.

These and other objects of the present invention, which will be apparent from the detailed description of the invention provided hereinafter, have been met, in one embodiment, by a *Vibrio cholera* ZOT receptor, wherein said receptor has a molecular weight of about 45 kDa and an N-terminal amino acid sequence selected from the group consisting of SEQ ID NO:1, SEQ ID NO:2 and SEQ ID NO:3.

In still another embodiment, the above-described objects of the present invention have been met by a method for screening for an antagonist of *Vibrio cholera* ZOT comprising the steps of:

(A) carrying out an affinity binding assay on a test compound using substantially pure *Vibrio cholera* ZOT receptor having a modular weight of about 45 kDa and an N-terminal amino acid sequence selected from the group consisting of SEQ ID NO:1, SEQ ID NO:2 and SEQ ID NO:3 as the capture ligand; and (B) carrying out an assay on said test compound so as to determine whether said test compound possesses ZOT biological activity, wherein when said test compound specifically binds to said *Vibrio cholera* ZOT receptor, but does not possess ZOT biological activity, said test compound is an antagonist of *Vibrio cholera* ZOT.

In still another embodiment, the above-described objects of the present invention have been met by a method for screening for an agonist of *Vibrio cholera* ZOT comprising the steps of:

(A) carrying out an affinity binding assay on a test compound using substantially pure *Vibrio cholera* ZOT receptor having a modular weight of about 45 kDa and an N-terminal amino acid sequence selected from the group consisting of SEQ ID NO:1, SEQ ID NO:2 and SEQ ID NO:3 as the capture ligand; and (B) carrying out an assay on said test compound so as to determine whether said test compound possesses ZOT biological activity, wherein when said test compound specifically binds to said *Vibrio cholera* ZOT receptor, and possesses ZOT biological activity, said test compound is an agonist of *Vibrio cholera* ZOT.

BRIEF DESCRIPTION OF THE DRAWINGS

FIG. 1 shows the effect of the PKC inhibitor CGP41251, and its inactive analogue CGP42700, on changes in tissue resistance (Rt) induced by pZ14 supernatant in rabbit ileum.

FIGS. 2A and 2B show the effect of ZOT on PKC activity over time in cytosolic (FIG. 2A), and membranous (FIG. 2B) subfractions.

FIG. 3 shows a dose-response curve for purified ZOT on Rt in rabbit ileum.

FIG. 4 shows the effect of purified MBP-ZOT (Δ) as compared to purified ZOT (□), and MBP control (■) on Rt in rabbit ileum.

DETAILED DESCRIPTION OF THE INVENTION

Figure 2B:
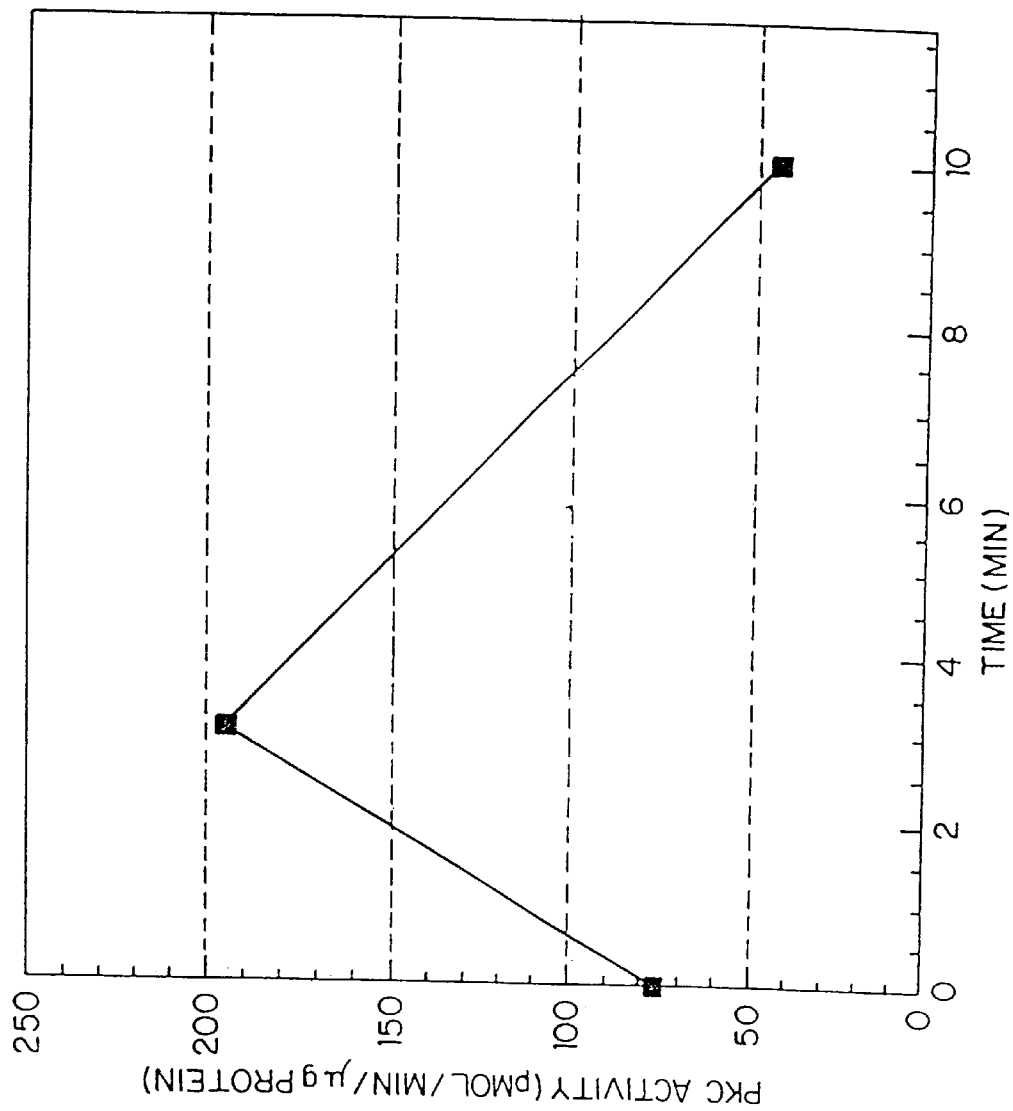

As discussed above, in one embodiment, the present invention relates to a *Vibrio cholera* ZOT receptor, wherein said receptor has a modular weight of about 45 kDa and an N-terminal amino acid sequence selected from the group consisting of SEQ ID NO:1, SEQ ID NO:2 and SEQ ID NO:3.

The ZOT receptor can be used to make antibodies, either polyclonal or monclonal, using techniques well-known in the art (Abrams, *Methods Enzymol.*, 121:107–119 (1986)).

Alternatively, the ZOT receptor can be used to purify, by affinity chromatography, ZOT, and fusions proteins thereof.

Moreover, the ZOT receptor can be used to screen for analogs of ZOT which are either antagonist or agonists.

Thus, in another embodiment, the above-described objects of the present invention have been met by a method for screening for an antagonist of *Vibrio cholera* ZOT comprising the steps of:

(A) carrying out an affinity binding assay on a test compound using substantially pure *Vibrio cholera* ZOT receptor as the capture ligand; and (B) carrying out an assay on said test compound so as to determine whether said test compound possesses ZOT biological activity, wherein when said test compound specifically binds to said *Vibrio cholera* ZOT receptor, but does not posses ZOT biological activity, said test compound is an antagonist for *Vibrio cholera* ZOT.

In another embodiment, the above-described objects of the present invention have been met by a method for screening for an agonist of *Vibrio cholera* ZOT comprising the steps of:

(A) carrying out an affinity binding assay on a test compound using substantially pure *Vibrio cholera* ZOT receptor as the capture ligand; and (B) carrying out an assay on said test compound so as to determine whether said test compound possesses ZOT biological activity, wherein when said test compound specifically binds to said *Vibrio cholera* ZOT receptor, and possesses ZOT biological activity, said test compound is an agonist for *Vibrio cholera* ZOT.

As used herein, "ZOT biological activity" means the ability to reversibly increase epithelial permeability by modulating the structure of intercellular tj.

The assay to determine ZOT biological activity is not critical to the present invention. For example, the assay may involve (1) assaying for a decrease of tissue resistance (Rt) of ileum mounted in Ussing chambers as described by Fasano et al, *Proc. Natl. Acad. Sci., USA*, 8:5242–5246 (1991); (2) assaying for a decrease of tissue resistance (Rt) of intestinal epithelia cell monolayers in Ussing chambers as described in Example 3 below; or (3) assaying for intestinal or nasal enhancement of absorption of a therapeutic agent, as described in WO 96/37196; U.S patent application Ser. No. 08/443,864, (U.S. Pat. No. 5,827,534) filed May 24, 1995; U.S. patent application Ser. No. 08/598,852, filed Feb. 9, 1996 (now U.S. Pat. No. 5,665,389); and U.S. patent application Ser. No. 08/781,057, filed Jan. 9, 1997.

Thus, the present invention also relates to antagonists of *Vibrio cholera* zonula occludens toxin obtainable by the above-described method.

Antagonists of ZOT can be used as anti-inflammatory drugs for the treatment of gastrointestinal conditions where an increased intestinal permeability has been described, e.g., in the treatment of inflammatory bowel diseases, protein loosing enteropathy, food allergies, and celiac disease.

Agonists of ZOT will rapidly open tj in a reversible and reproducible manner, and thus can be used as intestinal or nasal absorption enhancers of a therapeutic agent in the same manner as ZOT is used as intestinal or nasal absorption enhancers, as described in WO 96/3796 U.S. patent application Ser. No. 08/443,864, (U.S. Pat. No. 5,827,534) filed May 24, 1995; U.S. patent application Ser. No. 08/598,852, filed Feb. 9, 1996 (now U.S. Pat. No. 5,665,389); and U.S. patent application Ser. No. 08/781,057, filed Jan. 9, 1997.

Thus, the present invention also relates to agonists of *Vibrio cholera* zonula occludens toxin obtainable by the above-described method.

The following examples are provided for illustrative purposes only, and are in no way intended to limit the scope of the present invention.

EXAMPLE 1

Effect of ZOT on Enterocyte Cytoskeleton

In the small intestine (Madara et al, *J. Cell Biol.*, 97:125–136 (1983)) and in renal cells (Meza et al, *J. Cell Biol.*, 87:746–754 (1980)), pathophysiological alterations in cytoskeletal arrangement may produce major alterations in occluding tj resistance, charge selectivity, and structure. The response elicited by these specific perturbations consists of expansion of occluding tj structure, and changes in paracellular cation selectivity. These data suggest that the paracellular pathway may be regulated by intracellular events which produce phenotypic alterations in the cell surface structure that regulates Zo. However, the cascade of intracellular events leading to such tj modifications is still poorly defined.

A. The Effect of ZOT on Cytoskeletal Arrangement

To evaluate whether ZOT has an effect on cytoskeletal rearrangement, the $M_r > 10,000$ supernatant fraction obtained after culturing V. cholerae strain CVD110 transformed with plasmid pZ14 (hereinafter "pZ14 supernatant"), was tested on tissue cultures of IEC6 cells.

CVD110 is a *V. cholerae* (El Tor biotype) strain in which all known toxin genes (ctxA, zot and ace genes) have been deleted (Michalski et al, *Infect. Immun.*, G1:4462–4468 (1993)).

Plasmid pZ14 contains the zot gene transcribed by the inducible tac promoter. Plasmid pZ14 was constructed by digesting pBB241 with HindIII. pBB241 was obtained by cloning a ClaI-XbaI fragment containing the entire zot sequence into plasmid pUC19 (Baudry et al, *Infect. Immun.*, 60:428–434 (1992))). The 5' overhang was filled in with Klenow fragment, and the linearized plasmid was digested with XbaI, yielding a zot fragment of 1.5 kb. This fragment was cloned into vector pTTQ181 (Amersham, Arlington Heights, Ill.) which was modified by interruption of the $AmP^R$ gene by the $Kan^R$ cassette found in pHSG274 described in Maniatis et al, *Molecular Cloning, A Laboratory Manual*, Cold Spring Harbor (1989). That is, pTTQ181 was digested with EcoRI, filled in, and digested with XbaI. The 1.5 kb XbaI zot fragment was ligated into the resulting vector in the correct orientation, and was designated "pZ14".

The IEC6 cells were derived from crypt cells of germ-free rat small intestine (Quaroni et al, *In: Methods in Cell Biology*, Chapter 20, 21B:403–426 (1980)), and were grown in complete medium in cell-culture flasks (Falcon) at 37° C. in an atmosphere of 95% $O_2$/5% $CO_2$. The complete medium comprised Dulbecco's modified Eagle medium supplemented with 4.5 g/l glucose, and containing 5.0% (v/v) fetal bovine serum (irradiated), 10 $\mu$g/ml insulin, 4.0 mM L-glutamine, 50 U/ml penicillin, and 50 $\mu$g/ml streptomycin. The passage number used varied from between 15 and 20.

The $M_r$>10,000 supernatant fraction was prepared as follows. CVD110 transformed with pZ14 was cultured overnight at 37° C., in Luria Bertani (hereinafter "LB") broth containing 50 $\mu$g/ml kanamycin so as to select kanamycin-resistant strains harboring pZ14 plasmid. The cultures were then diluted to obtain an initial $OD_{600}$ of 0.4–0.5. Next, to induce expression of ZOT from the tac promoter, 2.0 mM of Isopropyl-Thio-$\beta$-D-Galactopyranoside (IPTG) (5'–3' Incorporation, Boulder, Colo.), was added to the cultures, which were incubated at 37° C. for another 2 hr. Next, the culture medium was collected, cooled and centrifuged at 5,000×g for 10 min at 4° C. The resulting liquid was collected and passed through a 0.45 $\mu$m filter (Millipore). The resulting culture supernatant was then subjected to ultrafiltration through Centricon filters (Vangard International Corp., N.J.) with a 10 kDa M cut-off size. The $M_r$>10 kDa fraction was washed twice with phosphate buffered saline (pH 7.4) (hereinafter "PBS"), reconstituted to the original volume in PBS, and tested for activity on cytoskeletal rearrangement as discussed below.

1. Fluorescent Microscopy $2.0 \times 10^4$ IEC6 cells/ml were seeded onto 13 mm diameter glass coverslips, and exposed to 30 $\mu$l of the pZ14 supernatant (1:33 dilution) or to 30 $\mu$l of PBS as a negative control, for 24 hr at 37° C. The cells were then fixed in 3.7% (v/v) formaldehyde in PBS (pH 7.4) for 10 min at room temperature. After washing in the same buffer, the cells were permeabilized with 0.5% (v/v) Triton X-100 (Sigma) in PBS (pH 7.4) for 10 min at room temperature. The resulting fixed cells were then incubated with 5.0 $\mu$g/ml fluorescein-phalloidin (Sigma) at 37° C. for 30 min. Finally, the cells were washed with PBS, the coverslips were mounted with 1:1 glycerol-PBS (pH 8.0), and 200 cells for each condition were analyzed in triplicate in blind fashion with a Nikon Optiphot fluorescence microscope so to visualize the F-actin cytoskeletal network (defined as stress fibers) of the cells.

The normal distribution of stress fibers was seen within the cells incubated with the PBS negative control. However, when the IEC6 cells were incubated with pZ14 supernatant, a complete rearrangement of the cytoskeleton was observed (peaking at 24 hr incubation), with the stress fibers redistributed to the cell periphery.

After 48 hr exposure to pZ14 culture supernatant, F-actin organization remained unchanged from the cells exposed for 24 hr. F-actin organization in the negative controls remained unchanged over the 48 hr study period.

2. Scanning Electron Microscopy

In parallel studies, the IEC6 cells incubated with pZ14 supernatant or PBS negative control were analyzed by scanning electron microscopy.

More specifically, IEC6 cells were seeded at $5.0 \times 10^9$ cells/well onto 13 mm diameter glass coverslips inserted in the wells of 24-well plates. After 24 hr exposure to either 30 $\mu$l of pZ14 supernatant or 30 $\mu$l of PBS negative control at 37° C., the cells were fixed with 2.5% (v/v) glutaraldehyde in 0.1 M cacodylate buffer (pH 7.4) for 20 min at room temperature. Following post-fixation in 1.0% (w/v) $OsO_4$ for 30 min, the cells were dehydrated through graded ethanols, critical point dried under $CO_2$, and gold coated by sputtering. The samples were examined with a Cambridge scanning electron microscope.

Modifications of the surface of ZOT-exposed cells were seen when compared to the PBS negative control. That is, ZOT mainly induced a loss of microvilli around the cell periphery with central sparing. These surface changes are consistent with the F-actin redistribution induced by ZOT seen in the fluorescent microscopy above.

3. Rabbit Ileum Studies

Experiments on cytoskeletal reorganization were then performed using rabbit ileum mounted in Ussing chambers as described by Fasano et al, Proc. Nat. Acad. Sci., USA, 8:5242–5246 (1991).

More specifically, 2–3 kg adult male New Zealand white rabbits were sacrificed by cervical dislocation. A 20 cm segment of ileum was removed, rinsed free of the intestinal content, opened along the mesenteric border, and stripped of muscular and serosal layers. Eight sheets of mucosa so prepared were then mounted in lucite Ussing chambers (1.12 $cm^2$ opening), connected to a voltage clamp apparatus (EVC 4000 WPI, Saratosa, Fla.), and bathed with freshly prepared Ringer's solution comprising 53 mM NaCl, 5.0 mM KCl, 30.5 mM mannitol, 1.69 mM $Na_2HPO_4$, 0.3 mM $NaH_2PO_4$, 1.25 mM $CaCl_2$, 1.1 mM $MgCl_2$, and 25 mM $NaHCO_3$. The bathing solution was maintained at 37° C. with water-jacketed reservoirs connected to a constant-temperature circulating pump and gassed with 95% $O_2$/5% $CO_2$.

300 $\mu$l of pZ14 supernatant was added to the mucosal side. 300 $\mu$l of pZ14 supernatant was also added to the serosal side to preserve the osmotic balance. The potential difference (PD) was measured every 10 min, and the short-circuit current (Isc) and tissue resistance (Rt) were calculated as described by Fasano et al, supra. Because of tissue variability, data were calculated as Rt (Rt at time x)–(Rt at time 0). At the end of every experiment, 0.5 mM glucose was added to the mucosal side of each chamber. Only those tissues which showed an increase in Isc in response to glucose (indicating tissue viability) were included in the analysis.

Once the maximum effect of ZOT on Rt was obtained after 60 min of incubation, the tissues exposed to either the pZ14 supernatant or the PBS negative control were fixed, and stained for F-actin with fluorescein-phalloidin, as described above.

Control rabbit ileum was characterized by homogeneous fluorescent staining of the brush border, and a columnar distribution of actin microfilaments between adjacent enterocytes. Rabbit ileum exposed to pZ14 supernatant showed an irregular staining of the brush border, associated with a partial redistribution of F-actin within the underlying cytoplasm. These changes were more evident in the mature cells of the tip of the villi as compared to the less differentiated crypt cells.

4. Evaluation of Actin Pools

Actin is one of the principal constituents of the cellular cytoskeletal network, and shifts between the soluble monomeric G-actin pool and filamentous F-actin pool reflects changes in actin organization (Drenchahn et al, J. Cell Biol., 107:1037–1048). Thus, the effect of ZOT on G- and F-actin pools was evaluated.

More specifically, bovine pulmonary artery endothelial cells (Goldblum et al, J. Cell Physiol., 157:197–205 (1993)), obtained from the American Type Culture Collection (Rockville, MD) ATCC No. 209CCL, were grown at 37° C. under 95% $O_2$/5% $CO_2$ in Dulbecco's modified Eagle's medium enriched with 20% (v/v) heat-inactivated (56° C., for 30 min) fetal calf serum (HyClone Laboratories, Logan Utah), 4.0 mM L-glutamine, non-essential amino acids, and vitamins in the presence of 50 U/ml penicillin and 50 $\mu$g/ml streptomycin. The cultures were determined to be endothelial by uniform morphology and by quantitative determination of angiotensin-converting enzyme activity with commercially available $^3$H-benzyl-Phe-Ala-Pro substrate (Ventrex Laboratories, Inc., Portland, Me.). Only cell passages 3–7 were used.

Endothelial F-actin was fluorometrically measured as described by Goldblum et al, supra. More specifically, $5.8\times10^5$ endothelial cells in 2.0 ml of Dulbecco's modified Eagle's medium enriched with 20% (v/v) heat-inactivated (56° C., 30 min) fetal calf serum (HyClone Laboratories, Logan, Utah), 4.0 mM L-glutamine, nonessential amino acids, and vitamins in the presence of 50 U/ml penicillin and 50 μg/ml of streptomycin, were seeded into the wells of 6-well plates and cultured for 72 hr at 37° C. in 95% $O_2$/5% $CO_2$. The monolayers were exposed to 30 μl of pZ14 supernatant (1:33 dilution) for 24 hr, after which they were washed twice in a buffer comprising 75 mM KCl, 3.0 mM $MgSO_4$, 1.0 mM ethylene glycol tetraacetic acid (EGTA), 10 mM imidazole, 0.2 mM dithiothreitol (DTT), 10 μg/ml aprotinin, and 0.1 mM phenylmethylsulfonyl fluoride (PMSF), and fixed with 3.7% (v/v) formaldehyde for 15 min. Next, the monolayers were permeabilized with 0.2% (v/v) Triton X-100 in the above buffer for 5 min at room temperature, stained with $1.65\times10^{-7}$ M NBD-phallicidin (Sigma) for 20 min, and extracted with ice cold methanol overnight at -20° C. Staining and extractions were performed in the dark. Extracts were harvested into curvettes and intraendothelial fluorescence was measured in a Perkin-Elmer LS30 luminescence spectrometer at room temperature at 465 nm excitation (10 nm slit) and 535 nm emission (10 nm slit), and expressed in arbitrary fluorescent units per mg total endothelial cell protein.

Application of NBD-phallicidin to fixed permeabilized endothelial monolayers resulted in 78.8% penetration of the probe into the cell, and 99.98% of intracellular probe was extracted with a single methanol treatment, as measured by fluorometry.

Actin reorganization can involve reciprocal changes in the soluble monomeric G- and filamentous F-actin pool, while the total actin pool remains unchanged. The above-described methodologies for determining F- and G-actin pools involve fixation, permeabilization, and extraction procedures which preclude protein determinations on the same bovine pulmonary artery endothelial monolayers. Therefore, for standardization of F- and G-actin measurements, additional simultaneously plated cells for total protein determination were cultured under identical conditions as the monolayers assayed for the F- and G-actin pools.

More specifically, post-confluent bovine pulmonary artery endothelial monolayers in the wells of 6-well plates were washed twice with PBS (pH 7.4) and gently detached by exposure to 0.5 mg/ml trypsin for 1–2 min with gentle agitation, followed immediately by neutralization with the Dulbecco's medium described above containing PBS. The cells were centrifuged at 600×g for 10 min at 4° C., again washed twice with PBS (pH 7.4), and lysed in lysing buffer comprising 3.0% (w/v) sodium dodecyl sulfate (SDS), 1.0 mM DTT, 10 mM PMSF, 1.0 mM ethylenediamine tetraacetic acid (EDTA), and 50 mM Tris-HCl (pH 8.0). The lysates were then assayed for protein concentration using the standard Bio-Rad DC Protein Assay (Bio-Rad Chemical Division, Richmond, Calif.).

Endothelial G-actin was measured using the DNAseI inhibition assay as described by Goldblum et al, supra. More specifically, bovine pancreas DNAseI (Sigma) was dissolved in 0.125 M Tris-HCl (pH 7.5) 5.0 MM $MgCl_2$, 2.0 mM $CaCl_2$, 1.0 mM $NaN_3$, and 0.1 mM PMSF at a concentration of 10 mg/ml so as to increase its stability. The stock solution was then diluted 100× with 20 mM imidazole (pH 7.5), 30 mM $NaCl_2$, and 15% (v/v) glycerol. The enzyme was freshly made every 2 hr and kept on ice. Calf thymus DNA (type 1, Sigma) was used as substrate for the DNAseI. The fibrous DNA preparation was cut into fine pieces and suspended in 0.1 M Tris-HCl (pH 7.5), 4.0 mM $MgSO_4$, 1.8 mM $CaCl_2$ at a concentration of 80 mg DNA/ml. The DNA was brought into solution by slow stirring at 4° C. for 48 hr, after which the solution was sequentially passed through 0.45 μm and 0.22 μm pore size filters, and stored at 4° C. The absorbance of the final substrate at 260 nm varied between 1.05 and 1.15. The DNAseI was then mixed with DNA substrate in the cuvette of a Gilford response spectrophotometer (Ciba Corning Diagnostics), and the slope of the linear portion of the OD at 260 nm recorded. Purified bovine skeletal muscle actin (Sigma) dissolved in 20 mM Tris-HCl (pH 7.5), 1.0 M Na acetate, 1.0 mM $CaCl_3$, 1.0 mM adenosine triphosphate (ATP), 0.75 M guanidine-HCl was used as the G-actin standard to calibrate the assay.

Bovine endothelial monolayers grown in 6-well plates were exposed to 30 μl of pZ14 supernatant. The monolayers were washed with Dulbecco's PBS without $Ca^{2+}$ and $Mg^{2+}$, and permeabilized with 0.5 ml/well of lysing buffer comprising Hanks Balanced Salt Solution containing 1.0% (v/v) Triton X-100, 2.0 mM $MgCl_3$, 2.0 mM EGTA, 0.2 mM ATP, 0.5 mM DTT, 0.1 mM PMSF for 5 min. The G-actin-containing supernatants then were tested in the DNAseI inhibition assay to generate inhibitory activities that fell on the linear portion of the standard curve, i.e., 30–70% inhibition. The inhibitory activities were interpolated to G-actin concentrations, which were used to calculate G-actin expressed in μg/mg total endothelial cell protein.

Monolayers exposed to 30 μl of pZ14 supernatant boiled for 15 min, so as abolish the effect of ZOT on Rt, and 30 μl of supernatant from V. cholera strain CVD110 (Michalski et al, supra) transformed with pTTQ181 (Amersham, Arlington Heights, Ill.) (hereinafter "pTTQ181 supernatant") were used as negative controls.

pZ14 supernatant induced a significant decrease in the G-actin pool (-27%), and a reciprocal increase in the F-actin pool (+22%) as compared to either pTTQ181 supernatant or pZ14-boiled supernatants (see Table I below). This G- to F-actin shift is compatible with actin polymerization. This effect was completely abolished by boiling the pZ14 supernatant for 15 min.

TABLE I

G- and F-Actin Assays and Effect of PKC Inhibitor CGP41251 on Actin Polymerization

| Strain (N)* | G-Actin (μg/mg protein) | p value** | F-Actin (U/mg protein) | p value** |
|---|---|---|---|---|
| PTTQ181 (20) | 106.1 (3.92)*** | — | 341.34 (5.28)*** | — |
| pZ14 (38) | 76.0 (4.16) | 0.0001 | 415.73 (22.03) | 0.0036 |
| CGP41251 + pZ14 (30) | 108.6 (7.2) | 0.7803 | 335.67 (12.1) | 0.673 |
| CGP42700 + pZ14 (30) | 84.8 (4.0) | 0.0011 | 446.17 (18.5) | 0.0001 |

*Number of experiments
**Compared to pTTQ181 negative control
***Standard Error (S.E.)

5. Effect of ZOT on F-actin and ZO-1 Protein Distribution

Parallel studies were conducted on the effect of ZOT on F-actin and ZO-1 protein distribution in IEC6 cells apically sectioned to include the tj complex.

More specifically, $2.0\times10^4$ IEC6 cells/ml cultured on coverslips were incubated at 37° C. for 24 hr with 30 μl of pZ14 supernatant. After the incubation, the cells were fixed in 3.7% (v/v) formaldehyde in PBS (pH 7.4) for 10 min at room temperature. After washing in the same buffer, the cells were permeabilized with 0.5% (v/v) Triton X-100 in PBS (pH 7.4) for 10 min at room temperature. The cells were then incubated with both 5.0 μg/ml fluorescein-phalloidin and 2.0 μg/ml anti-ZO-1 antibody 7445 (Zymed laboratory Inc, South San Francisco, Calif.) at 37° C. for 30 min. Finally, the cells were washed with PBS (pH 7.4), the coverslips were mounted with glycerol-PBS (1:1 dilution) (pH 8.0), and 200 cells for each condition were analyzed in triplicate in blind fashion with a Nikon Optiphot fluorescence microscope. The results were expressed in terms of percentage of cells showing cytoskeleton rearrangement.

As a negative control, the complex network of F-actin filaments of IEC6 cells (stained with fluorescein-phalloidin) were incubated for 24 hr with 30 μl of pTTQ181 supernatant.

Immunofluorescence localization of ZO-1 within the same cells probed with anti-ZO-1 antibody 7445, which recognizes both ZO-1 isoenzymes, showed uniform continuous staining of ZO-1 exclusively along the cell-cell boundaries. On the contrary, pZ14 supernatant induced loss of centrally located, transcytoplasmatic actin filaments, as well as redistribution of ZO-1 from the cell-cell interface. The redistribution of ZO-1 protein from the tj complex was not associated to its tyrosine phosphorylation.

Taken together, these results indicate that actin polymerization induced by ZOT is mechanistically linked to the redistribution of the ZO-1 protein from the tj complex. Therefore, ZO-1 may be one link between ZOT-induced actin reorganization and the opening of the tj.

EXAMPLE 2

Intracellular Mediator of ZOT

Several intracellular mediators have been mechanistically linked to changes in tj permeability, including cAMP, $Ca^{++}$, and PKC (Madara, supra; and Balda et al, *J. Membrane Biol.*, 122:193–202 (1991)). However, the observation that the response to theophylline (a phosphodiesterase inhibitor) in rabbit ileum pre-exposed to *V. cholerae* 395 supernatant (containing both CT and ZOT) induced a peak response in Isc similar to that evoked in tissues exposed to the negative control, suggests that ZOT-induced changes in tissue permeability are not mediated through cAMP (Fasano et al, supra). Similar results were obtained when ZOT-containing supernatants were tested alone or in combination with purified CT. These results suggest that the total amounts of intracellular cAMP in control or ZOT-exposed tissues are comparable. Thus, to determine whether PKC mediates ZOT activity, rabbit small intestines and IEC6 cells were exposed to the PKC inhibitor staurosporine (MacLeod et al, *Amer. Physiol. Soc.*, 192:C950–C955 (1992)).

A. Rabbit Small Intestines

More specifically, rabbit ileum stripped of the muscular and serosal layers was mounted in Ussing chambers, and then exposed to 300 μl (1:33 dilution) of pZ14 supernatant, either alone or in combination with 10 nM staurosporine, added 10 min prior to and throughout the pZ14 supernatant exposure. Changes in Rt where then recorded at 10 min intervals.

10 nM staurosporine was found to completely prevent the decrease of Rt induced by pZ14 supernatant. Since staurosporine is a potent, but non-selective inhibitor of PKC activity (Meyer et al, *Int. J. Cancer*, 43:851–856 (1989)), a staurosporine derivative, i.e., CGP41251 that selectively inhibits PKC (Meyer et al, supra), was then tested on ZOT-induced actin reorganization and tissue permeability.

More specifically, rabbit ileum stripped of the muscular and serosal layers was mounted in Ussing chambers and then exposed to 300 μl (1:33 dilution) pZ14 supernatant, either alone or in combination with 10 nM CGP41251, added 10 min prior to and throughout the pZ14 supernatant exposure. Ussing chambers pre-exposed to 10 mM of an inactive staurosporine analogue, i.e., CGP42700 (Meyer et al, supra) for 10 min and throughout the pZ14 supernatant exposure were used as negative controls. Changes in Rt where then recorded at 10 min intervals. The results are shown in FIG. 1.

As shown in FIG. 1, pre-treatment with 10 nM CGP41251, but not with its inactive analogue CGP47200, prevented the changes in Rt induced by pZ14 supernatant. No significant changes were observed when the tissues were exposed in a similar manner to pTTQ181 supernatant.

Phorbol esters are a PKC activator. Thus, the phorbol ester 12-tetradecanoylphorbol-13-acetate (TPA) was tested to confirm that ZOT acts via PKC.

More specifically, rabbit ileum stripped of the muscular and serosal layers was mounted in Ussing chambers and then exposed to 300 μl (1:33 dilution) pZ14 supernatant, either alone or in combination with $10^{-8}$ M TPA added 10 min prior to and throughout the pZ14 supernatant exposure. Changes in Rt where then recorded at 10 min intervals.

A significant reduction in Rt was induced with pZ14 supernatant when compared to pTTQ181 supernatant (−7.33 Å 2.55 vs −2.57 Å 1.51 mohms.cm$^2$; p<0.005). When added to the same tissue, TPA together with pZ14 supernatant produced a decrease in Rt (total Rt change: −7.37 Å 3.2 mohms.cm$^2$) which is not different from that seen with TPA alone. These results demonstrate that the effect of ZOT and TPA on intestinal permeability is non-additive, suggesting that they both act through PKC.

B. IEC6 Cells

The effect of ZOT on the actin cytoskeleton of IEC6 cells in the presence of PKC inhibitors was then evaluated.

More specifically, $2.0 \times 10^5$ IEC6 cells were pre-treated with either 10 nM CGP41251 or 10 nM CGP42700 for 30 min prior to and throughout exposure to 30 μl of pZ14 supernatant. After 24 hr incubation at 37° C., $2.0 \times 10_4$ IEC6 cells/ml, cultured on coverslips, were fixed in 3.7% (v/v) formaldehyde in PBS (pH 7.4) for 10 min at room temperature. After washing in the same buffer, the cells were permeabilized with 0.5% (v/v) Triton X-100 in PBS (pH 7.4) for 10 min at room temperature. The cells were then incubated with 5.0 μg/ml fluorescein-phalloidin at 37° C. for 30 min. Finally, the cells were washed with PBS (pH 7.4), the coverslips were mounted with glycerol-PBS (1:1 dilution) (pH 8.0), and 200 cells for each condition were analyzed in triplicate in blind fashion with a Nikon Optiphot fluorescence microscope. The results were expressed in terms of the percentage of cells showing cytoskeleton rearrangement.

When pZ14 supernatant was added, 62% of the cells showed a rearrangement of the cytoskeleton, while only 27% of the cells exposed to PBS, and 21% of cells exposed to pTTQ181 supernatants were affected. Pre-treatment with 10 nM of CGP41251, but not with 10 nM of its inactive analogue CGP42700, blocked the cytoskeletal effects of ZOT (31% vs 58% of cells affected, respectively).

Moreover, ZOT-induced actin polymerization, i.e., a decrease in G- and an increase in F-actin pools was significantly blocked when bovine pulmonary artery endothelial cells were tested as described above, and pre-treated with 10 nM of CGP412512, whereas pre-treatment with 10 nM of CGP42700 did not cause such blockage (see Table I above).

These combined data indicate that ZOT activates PKC, and that this activation occurs proximally to both actin polymerization and final opening of tj.

C. The PKC State

PKC exists in two states in all cells, i.e., an inactive state in which the kinase is associated with the cytoplasm, and an active state in which the molecule is translocated from the cytoplasm to the membranes (Thomas et al, *Methods Enzymol.*, 1410:399–435 (1987)). Thus, the state of PKC was directly measured in IEC6 cells exposed to pZ14 supernatant.

More specifically, confluent IEC6 monolayers were treated with 30 µl of pZ14 supernatant (1:33 dilution) for increasing time intervals (0, 3 min, 10 min). After ZOT exposure, the IEC6 cells were lysed by mechanic disruption (forced passage through 25 gauge needle 3 times), the cytoplasmic and membrane fractions were separated by centrifugation at 13,000×g for 30 min at 4° C., and assayed for PKC activity by determining the incorporation of $^{32}P$ from $[\gamma^{-32}P]$ ATP into histone 1 (Ellis et al, *Am. J. Physiol.* 263:F293–F300 (1992)). As a control, PKC activity was also determined using a PKC assay system (Gibco BRL, Grand Island, N.Y.) based on measurement of the phosphorylation of acetylated myelin basic protein as described by Yasuda et al, *Biochem. Biophys. Res. Commun.*, 166:1220 (1990). The net PKC activity value reflects the difference between PKC activity in the presence and absence of PKC 19–26, a PKC pseudosubstrate inhibitor (Yasuda et al, supra). Total PKC specific activity (pmol/min) was normalized to total protein. The results are shown in FIGS. 2A–2B.

As shown in FIGS. 2A–2B, pZ14 supernatant induced a significant (1.72-fold) increase of membranous (FIG. 2B), and, to a lesser extend, cytosolic (FIG. 2A), PKC activity. In an average of 3 experiments, this ZOT-induced PKC activity increase peaked at 3 min (134.0 pmol/min/mg protein vs. baseline value of 77.6 pmol/min/mg protein) and returned to baseline at 10 min (65.4 pmol/min/mg protein). These data directly demonstrate that ZOT effect on tissue permeability is mediated by PKC.

D. PKC Isoenzyme

Molecular cloning and sequence analysis of PKC has demonstrated the existence of a gene family encoding several closely related, but distinct, isoenzymes with different physiological properties (Azzai et al, *Eur. J. Biochem.*, 208:547–557 (1992)). Staurosporine and its more specific derivative CGP41251 preferentially inhibit the $Ca^{2+}$-dependent group-A PKC isoenyzmes as compared to the $Ca^{2+}$-independent group-B isoenzymes (McGlynn et al, *J. Cell Biochem.*, 49:239–250 (1992); and Marte et al, *Cell Growth and Differ.*, 5:239–247 (1994)). As a result, experiments focusing on PKC-α, the only detectable $Ca^{2+}$-dependent PKC isoenzyme described in ileal enterocytes (Hyun et al, *Comp. Biochem. Physiol.*, 108C:171–178 (1994)), were carried out.

More specifically, 15–30 µg protein/lane cytosolic membrane fractions obtained as described above were separated by 8.0% (w/v) SDS-PAGE. Separated proteins were transferred to a nylon membrane (N-Immobilon, Millipore) in a Trans-Blot Electrophoretic Transfer Cell (Bio-Rad). The membrane was rinsed in PBS containing 0.05% (v/v) Tween 20 (hereinafter "PBS-T"), and blocked in PBS-T containing 5.0% (v/v) non-fat milk for 1 hr at room temperature. Affinity-purified anti-PKC-α and anti-PKC-antibodies (Gibco BRL) were diluted to obtain optimal saturating conditions (1:500 dilution) in PBS-T containing 0.83% (v/v) non-fat milk, and incubated with the membrane for 16 hr at 4° C. Following incubation, the membrane was first washed with 5.0% (v/v) non-fat milk in PBS-T (3× for 15 min), then with PBS-T (1× for 15 min), and incubated for 2 hr at room temperature with a 1:30,000 dilution of goat anti-rabbit IgG conjugated to horseradish peroxidase. Following extensive washing with 5.0% (v/v) non-fat milk in PBS-T, immunoreactive bands were developed using enhanced chemiluminescence (Amersham).

Isoform-specific synthetic peptides (Gibco BRL) having the amino acid sequences for each respective PKC isoform were used as controls. The synthetic peptides were based on unique sequences in the $V_3$ region of α-PKC:
(Ala-Gly-Asn-Lys-Val-Ile-Ser-Pro-Ser-Glu-Asp-Arg-Arg-Gln, SEQ ID NO:4), and
$V_3$ region of ε-PKC:
(Lys-Gly-Phe-Ser-Tyr-Phe-Gly-Glu-Asp-Leu-Met-Pro, SEQ ID NO:5).

As determined by immunoblotting, acute (3 min) treatment of IEC6 cells with pZ14 supernatant induced a significant translocation of PKC-α isoenzyme from the cytosol to the membrane of the cells. This reduction was partially reversed after 10 min of incubation. $10^{-7}$ M TPA induced a similar, but more sustained (up to 2 hr) reduction of cytosolic PKC-α, whereas down-regulation of this isoform was observed after 24 hr incubation. A continuous, time-dependent accumulation of the PKC-α regulatory subunit was observed in the cellular cytosol. No significant increase in PKC-α was detected in either membrane fractions obtained from cells exposed to pZ14 supernatant or the TPA positive control.

These results provide strong evidence that PKC-α is the intracellular mediator of ZOT-induced actin reorganization and tj disassembly.

E. Serine Phosphorylation

Experiments in IEC6 cells were also conducted to determine serine phosphorylation of target protein(s) in both cellular membrane or cytosolic subfractions in order to identify the substrate of PKC phosphorylation.

More specifically, $2.0\times10^5$ IEC6 cells/wells were exposed to $10^{-10}$ M purified MBP-ZOT (obtained in Example 5), at increasing time intervals (0, 15 min, 30 min, 45 min). The reaction was stopped with cold PBS (pH 7.4) (washed three times), and the cells were scraped and lysed as described above. Cytosolic and membranous subfractions were then obtained as described above. 20–30 µg of each preparation were separated by 8.0% (w/v) SDS-PAGE. Separated proteins were transferred to a nylon membrane (N-Immobilon, Millipore) in a Trans-Blot Electrophoretic Transfer Cell (Bio-Rad). The membrane was rinsed and blocked in PBS-T containing 5.0% (v/v) non-fat milk for 1 hr at room temperature. Monoclonal anti-serine antibodies (Sigma Immunochemicals) were diluted to obtain optimal saturating conditions (1:1000 dilution) in PBS-T containing 0.83% (v/v) non-fat milk, and incubated with the membrane for 16 hr at 4° C. Following incubation, the membrane was first washed with 5.0% (v/v) non-fat milk in PBS-T (3× for 15 min), then with PBS-T (1× for 15 min), and incubated for 2 hr at room temperature with a 1:30,000 dilution of goat anti-rabbit IgG antibodies conjugated to horseradish peroxidase. Following extensive washing with 5.0% (v/v) non-fat milk in PBS-T, immunoreactive bands were developed using enhanced chemiluminescence (Amersham).

The results showed that purified MBP-ZOT induced time-dependent serine phosphorylation of a cytoplasmic protein of an apparent MW of 100–120 kDa. This protein may represent the target of PKC phosphorylation induced by ZOT, and may be involved in the intracellular signaling leading to the opening of tj.

EXAMPLE 3

Selectivity of ZOT Action

To establish an optimal in vitro system to study the effect of ZOT on tj, several cell lines were screened for ZOT responsiveness. This is because the Ussing chamber assay, while sensitive, is not suitable for screening a large number of samples. In search of an alternative system, a tissue culture assay for ZOT was developed.

A. Specific Effect of ZOT on Different Cell Lines

To establish whether ZOT exerts either a selective or a broad effect on tj regulation, several cell lines were tested for ZOT responsiveness. More specifically, human colon carcinoma cell lines HT-29 Cl 19A (Van Den Berghe et al, *Biochem. J.*, 258:673–679 (1992)), and CaCo2 (Nath et al, *J. Diarrhoeal Dis.*, 8:133–142 (1990)), were grown in cell-culture flasks (Falcon) under humidified atmosphere of 95% $O_2$/5% $CO_2$ at 37° C. in Dulbecco's modified Eagle's medium containing 10% (v/v) fetal-calf serum, 40 μg/l penicillin and 90 μg/l streptomycin. The cells were subcultured at a surface ratio of 1:5 after trypsin treatment every 5 days, when they had reached 70–80% confluence. The passage number of the cells used in the this study varied between 15 and 30.

The HT-29 Cl 19A or CaCo2 monolayers were grown to confluence (12–14 days after plating at a 1:2.5 surface ratio) on tissue-culture-treated polycarbonate filters firmly attached to a polystyrene ring (6.4 mm diameter, Transwell Costar). The filters were placed in a tightly fitting insert separating the serosal and mucosal compartment of a modified Ussing chamber, and the experiments were carried out as described above for the rabbit intestine.

No significant changes of Rt in HT-29 Cl 19A monolayers (n=4 for up to 3 hr each sample tested) exposed to 30 μl of pZ14 supernatant (1:33 dilution) were obtained when compared to monolayers exposed to 30 μl of pTTQ181 supernatant negative control. On the other hand, when tested in CaCo2 cell monolayers, 30 μl of pZ14 supernatant induced a significant decrease in Rt, suggesting a different susceptibility to ZOT between these two cell lines.

B. F-actin Organization

To study the effect of ZOT on F-actin organization, IEC6 and LLC-$PK_1$ (Hull et al, *In Vitro*, 12:670–677 (1976)) cell cultures were tested in the same manner.

The LLC-PK, i.e., pig kidney cortex, cells (Hull et al, supra) were grown in cell-culture flasks (Falcon) at 37° C. in an atmosphere of 95% O/5% $CO_2$. The culture medium consisted of Dulbecco's modified essential medium supplemented with 10% (v/v) fetal bovine serum. Cells ranging from passage 185 to 200 were passed weekly by trypsinizing with 0.25% (w/v) trypsin in 0.02% (w/v) EDTA, when they had reached 70–80% confluent monolayers.

IEC6 cells exposed to 30 μl of pZ14 supernatant, and subsequently probed with fluorescein-phalloidin, as described above, for F-actin, showed significant actin reorganization, while no significant changes were detected for LLC-$PK_1$ cells.

The observation that ZOT exerts a selective permeabilizating effect (probably interacting with a specific cellular receptor present only on "sensitive" cells), combined with its effect on cytoskeleton and the activation of PKC, indicates that ZOT acts via an intracellular pathway, rather then directly on tj.

EXAMPLE 4

Role of Phospholipase C in ZOT Activity

Phospholipase C (hereinafter "PLC") is an enzyme that converts phosphatidyl inositol diphosphate (hereinafter "$PIP_2$") into inositol triphosphate (hereinafter "$IP_3$") plus diacylglycerol (hereinafter "DAG"). PLC may participate in the assembly and sealing of ZOs, as well as in their regulation. The effect of PKC on ZOs is secondary to the activation of PKC induced by both $IP_3$ (via $Ca^{2+}$) and DAG (Berridte et al, *Nature*, 341:197–205 (1989)).

The effect of ZOT on cytoskeletal rearrangement, actin polymerization, and tissue permeability changes has been shown above to involve PKC activation. To establish whether the primary target of ZOT is PKC or PLC, the experiments in IEC6 cells and Ussing chambers described in Example 1 above were repeated, but the samples were pre-incubated for 10 min with 100 mM neomycin sulfate, and throughout the exposure to the pZ14 supernatant. Neomycin is a substance that binds to $PIP_2$, and prevents its conversion to $IP_3$ plus DAG by PLC.

IEC6 cell cultures pre-treated with 100 mM neomycin, and then exposed to pZ14 supernatant showed a lower percentage of cells presenting cytoskeletal rearrangement (12.0 Å 5.17) as compared to those exposed only to ZOT (49.0 Å 9.23; p<0.05). Pre-exposure of rabbit ileum to 100 mM neomycin sulfate partially prevented the increased tissue permeability induced by ZOT in untreated tissues.

These results indicate that the transmembrane PLC may play a role in ZOT-induced actin reorganization and tissue permeability.

EXAMPLE 5

Purification of ZOT 5000 ml of pZ14 supernatant was concentrated 1000-fold using a lamina flow filter with a MW cutoff of 10 kDa, and then subjected to 8.0% (w/v) SDS-PAGE. Protein bands were detected by Coomassie blue staining of the SDS-PAGE gel. No protein band corresponding to ZOT was detectable when compared to control pTTQ181 supernatant treated in the same manner. Therefore, even though the zot gene was placed behind the highly inducible and strong tac promoter in pZ14, the level of the protein in 1000-fold concentrated pZ14 supernatant was still not detectable by the Coomassie stained SDS-PAGE gel.

A. MBP-ZOT

To increase the amount of ZOT produced, the zot gene was fused in frame with the maltose binding protein (hereinafter "MBP") gene to create a MBP-ZOT fusion protein.

The MBP vector pMAL-c2 (Biolab) was used to express and purify ZOT by fusing the zot gene to the male gene of *E. coli*. This construct uses the strong, inducible tac promoter, and the malE translation initiation signals to give high level expression of the cloned zot gene. The vector pMAL-c2 has an exact deletion of the malE signal sequence, which leads to cytoplasmic expression of the fusion protein. Affinity chromatography purification for MBP was used to facilitate isolation of the fusion protein (Biolab).

More specifically, vector pMAL-c2 was linearized with EcoRI (that cuts at the 3' end of the male gene), filled in with Klenow fragment, and digested with XbaI (that has a single site in pMAL-c2 polylinker). The orf encoding ZOT was subcloned from plasmid pBB241 (Baudry et al, supra). Plasmid pBB241 was digested with BssHII, filled in with Klenow fragment, and digested with XbaI. Then, the blunt-XbaI fragment was subcloned into pMAL-c2 to give plasmid pLC10-c. Since both the insert, and the vector had blunt and sticky ends, the correct orientation was obtained with the 3' end of male fused with the 5' terminus of the insert.

pLC10-c was then electroporated into *E. coli* strain DH5α. In pBB241, the BssHII restriction site is within the zot orf. Thus, amino acids 1–8 of ZOT are missing in the MBP-ZOT fusion protein.

In order to purify the MBP-ZOT fusion protein, 10 ml of Luria Bertani broth containing 0.2% (w/v) glucose and 100 μg/ml ampicillin were inoculated with a single colony containing pLC10-c, and incubated overnight at 37° C. with shaking. The culture was diluted 1:100 in 1.0 ml of the same fresh medium, and grown at 37° C. while shaking, to about $1.0 \times 10^8$ cells/ml. 0.2 mM IPTG was then added to induce the MBP-ZOT expression, and the culture was incubated at 37° C. for additional 3 hr. The bacteria were then pelleted and resuspended in 20 ml of ice cold "column buffer" comprising 20 mM Tris-HCl, 0.2 M NaCl, 1.0 mM EDTA, 10 mM 2-ME, 1.0 mM $NaN_3$. The bacterial suspension was lysed by french press treatment and spun for 30 min at 13,000×g at 4° C. The supernatant was collected, diluted 1:5 with column buffer and loaded into a 1×10 column of amylose resin (Biolabs, MBP-fusion purification system), pre-equilibrated with column buffer. After washing the column with 5 volumes of column buffer, the MBP-ZOT fusion protein was eluted by loading 10 ml of 10 mM maltose in column buffer. The typical yield from 1.0 ml of culture was 2–3 mg of protein.

The MBP fusion partner of the purified MBP-ZOT fusion protein was then cleaved off using 1.0 μg of Factor Xa protease (Biolabs) per 20 μg of MBP-ZOT. Factor Xa protease cleaves just before the amino terminus of ZOT. The ZOT protein so obtained was run on a 8.0% (w/v) SDS-PAGE gel, and electroeluted from the gel using an electroseparation chamber (Schleicher & Schuell, Keene, N.H.).

When tested in Ussing chambers, the resulting purified ZOT induced a dose-dependent decrease of Rt, with an $ED_{50}$ of $7.5 \times 10^{-8}$ M (FIG. 3).

B. 6xHis-ZOT

The zot gene was amplified by PCR with Deep Vent polymerase (New England Biolabs), using pBB241 plasmid (Baudry et al, supra) DNA as a template. The forward and reverse primers used were: 5'-CGGGATCCCGTATGAGTATCTTT-3' (SEQ ID NO:6); and 5'-CCCAAGCTTGGGTCAAAATATACT-3' (SEQ ID NO:7), respectively. The 5' tails of these oligonucleotides contain a BamHI and a HindIII restriction site, respectively. The resulting amplicon (1.2 kb) was analyzed by 8.0% (w/v) agarose gel electrophoresis, and purified from salts and free nucleotides using an Xtreme spin column (Pierce). The above-noted two restriction enzymes were then used to digest the purified amplicon, and the resulting digested-amplicon was then inserted in the vector pQE30 (Quiagen), which had been previously digested with BamHI and HindIII, so as to obtain plasmid pSU113. pQE30 is an expression vector that provides high level expression of a recombinant protein with a 6 poly-histidine tag (6xHis). The expression product of plasmid pSU113 is therefore a 6xHis-ZOT fusion protein. pSU113 was then transformed into *E. coli* DH5α.

In order to purify the 6xHis-ZOT fusion protein, the resulting transformed *E. coil* were grown overnight at 37° C. in 150 ml of Luria Bertani broth containing 2.0% (w/v) glucose, 25 μg/ml of kanamycin and 200 μg/ml of ampicillin until the $A_{600}$ was about 1.10. Next, 75 ml of the overnight cultures were added to 1000 ml of Luria Bertani broth containing 2.0% (w/v) glucose, 25 μg/ml of kanamycin and 200 μg/ml of ampicillin, incubated for about 3 hrs at 37° C., with vigorous shaking, until the $A_{600}$ was about 0.7–0.9. Then, IPTG was added to a final concentration of 2.0 mM, and growth was allowed to continue for 5 hrs at 37° C. Next, the cells were harvested by centrifugation at 4000×g for 20 min, the cells resuspend in 5.0 ml/g wet weight of buffer A comprising 6.0 M GuHCl, 0.1 M sodium phosphate, and 0.01 M Tris-HCl (pH 8.0), and stirred for 1 hr at room temperature. Then, the mixture was centrifuged at 10,000×g for 30 min at 4° C., and to the resulting supernatant was added 4.0–5.0 ml/g wet weight of a 50% slurry of SUPER-FLOW resin (QIAGEN), and stirring was carried out for 1 hr at room temperature. The resulting resin was loaded into a 1.6×8.0 column, which was then washed sequentially with buffer A, buffer B comprising 8.0 M urea, 0.1 M sodium phosphate, and 0.01 M Tris-HCl (pH 8.0) and buffer C comprising 8.0 M urea, 0.1 M sodium phosphate, and 0.01 M Tris-HCl (pH 6.3). Each wash was carried out until the $A_{600}$ of the flow-through was less than 0.01. The 6xHis-ZOT fusion protein was eluted from the column using 20 ml of buffer C containing 250 mM imidazole. Then, the fractions containing with the 6xHis-ZOT fusion protein were checked by SDS-PAGE using the procedure described by Davis, *Ann. N.Y. Acad. Sci.*, 121:404 (1964), and the gel stained with Comassie blue. The fractions containing 6xHis-ZOT fusion protein were dialyzed against 8.0 M urea, combined, and then diluted 100 times in PBS. Next, 4.0 ml of a 50% slurry of SUPERFLOW resin was added, stirring was carried out for 2 hrs at room temperature, and the resulting resin loaded into a 1.6×8.0 column, which was then washed with 50 ml of PBS. The 6xHis-ZOT fusion protein was eluted from the column with 10 ml of PBS containing 250 mM imidazole. The resulting eluant was dialyzed against PBS, and the 6xHis-ZOT fusion protein was checked by SDS-PAGE, as described above.

EXAMPLE 6

Production of Anti-ZOT Antiserum

To obtain specific antiserum, a chimeric glutathione S-transferase (GST)-ZOT protein was expressed and purified.

More specifically, oligonucleotide primers were used to amplify the zot orf by polymerase chain reaction (PCR) using plasmid pBB241 (Baudry et al, supra) as template DNA. The forward primer (TCATCACGGCGCGCCAGG, SEQ ID NO:8) corresponded to nucleotides 15–32 of zot orf, and the reverse primer (GGAGGTCTAGAATCTGCCCGAT, SEQ ID NO:9) corresponded to the 5' end of ctxA orf. Therefore, amino acids 1–5 of ZOT were missing in the resulting fusion protein. The amplification product was inserted into the polylinker (SmaI site) located at the end of the GST gene in pGEX-2T (Pharmacia, Milwaukee, Wis.). pGEX-2T is a fusion-protein expression vector that expresses a cloned gene as a fusion protein with GST of *Schistosoma japonicum*. The fusion gene is under the control of the tac promoter. Upon induction with IPTG, derepression occurs and GST fusion protein is expressed.

The resulting recombinant plasmid, named pLCll, was electroporated in *E. coli* DH5α. In order to purify GST-ZOT fusion protein, 10 ml of Luria Bertani broth containing 100 μg/ml ampicillin were inoculated with a single colony containing pLC11, and incubated overnight at 37° C. with shaking. The culture was diluted 1:100 in 1.0 ml of the same fresh medium and grown at 37° C. while shaking, to about $1.0 \times 10^8$ cells/ml. 0.2 mM IPTG was then added to induce the GST-ZOT expression, and the culture was incubated at 37° C. for additional 3 hr. The bacteria were then pelleted, resuspended in 20 ml of ice cold PBS (pH 7.4)and lysed by the french press method. The GST-ZOT fusion protein was not soluble under these conditions as it sedimented with the bacterial pellet fraction. Therefore, the pellet was resuspended in Laemli lysis buffer comprising 0.00625 M Tris-HCl (pH 6.8), 0.2 M 2-ME, 2.0% (w/v) SDS, 0.025% (w/v) bromophenol blue and 10% (v/v) glycerol, and subjected to electrophoresis on a 8.0% (w/v) PAGE-SDS gel, and stained with Coomassie brilliant blue. A band of about 70 kDa (26 kDa of GST+44 kDA of ZOT), corresponding to the fusion protein, was electroeluted from the gel using an electroseparation chamber (Schleicher & Schuell, Keene, N.H.).

10 $\mu$g of the resulting eluted protein (10–20 $\mu$g) was injected into a rabbit mixed with an equal volume of Freund's complete adjuvant. Two booster doses were administered with Freund's incomplete adjuvant four and eight weeks later. One month later the rabbit was bled.

To determine the production of specific antibodies, $10^{-10}$ M of ZOT, along with the two fusion proteins MBP-ZOT and GST-ZOT, was transferred onto a nylon membrane and incubated with a 1:5000 dilution of the rabbit antiserum overnight at 4° C. with moderate shaking. The filter was then washed 15 min 4 times with PBS-T, and incubated with a 1:30,000 dilution of goat anti-rabbit IgG conjugated to horseradish peroxidase for 2 hr at room temperature. The filter was washed again for 15 min 4 times with PBS containing 0.1% (v/v) Tween, and immunoreactive bands were detected using enhanced chemiluminescence (Amersham).

On immunoblot, the rabbit antiserum was found to recognize ZOT, as well as MBP-ZOT and GST-ZOT fusion proteins, but not the MBP negative control.

Moreover, to confirm the production of appropriate anti-ZOT antibodies, neutralization experiments were conducted in Ussing chambers. When pre-incubated with pZ14 supernatant at 37° C. for 60 min, the ZOT-specific antiserum (1:100 dilution), was able to completely neutralize the decrease in Rt induced by ZOT on rabbit ileum mounted in Ussing chambers.

EXAMPLE 7

Purification of ZOT Receptors
A. Binding Studies

MBP-invasin fusion protein of *Yersinia pseudotuberculosis* is capable of binding to the integrin receptor of mammalian cells, and confers the invasive phenotype on non-pathogenic *E. coli* harboring plasmids that produce the MBP-invasin fusion protein (Leong et al, *The EMBO J.*, 9(6):1979–1989 (1990)). As a result, experiments were carried out to determine if the MBP-ZOT fusion protein, obtained in Example 5 above, recognizes a specific intestinal binding site, as well as to retain the ability to increase tissue permeability.

More specifically, rabbit ileum was stripped of the muscular and serosal layers, mounted in Ussing chambers, and then exposed to either $10^{-10}$ M purified MBP-ZOT or purified ZOT, both added to the mucosal side of the tissue. $10^{31\ 10}$ M MBP was used as a negative control. Changes in Rt where then recorded at 10 min intervals. The results are shown in FIG. 4.

Figure 4:
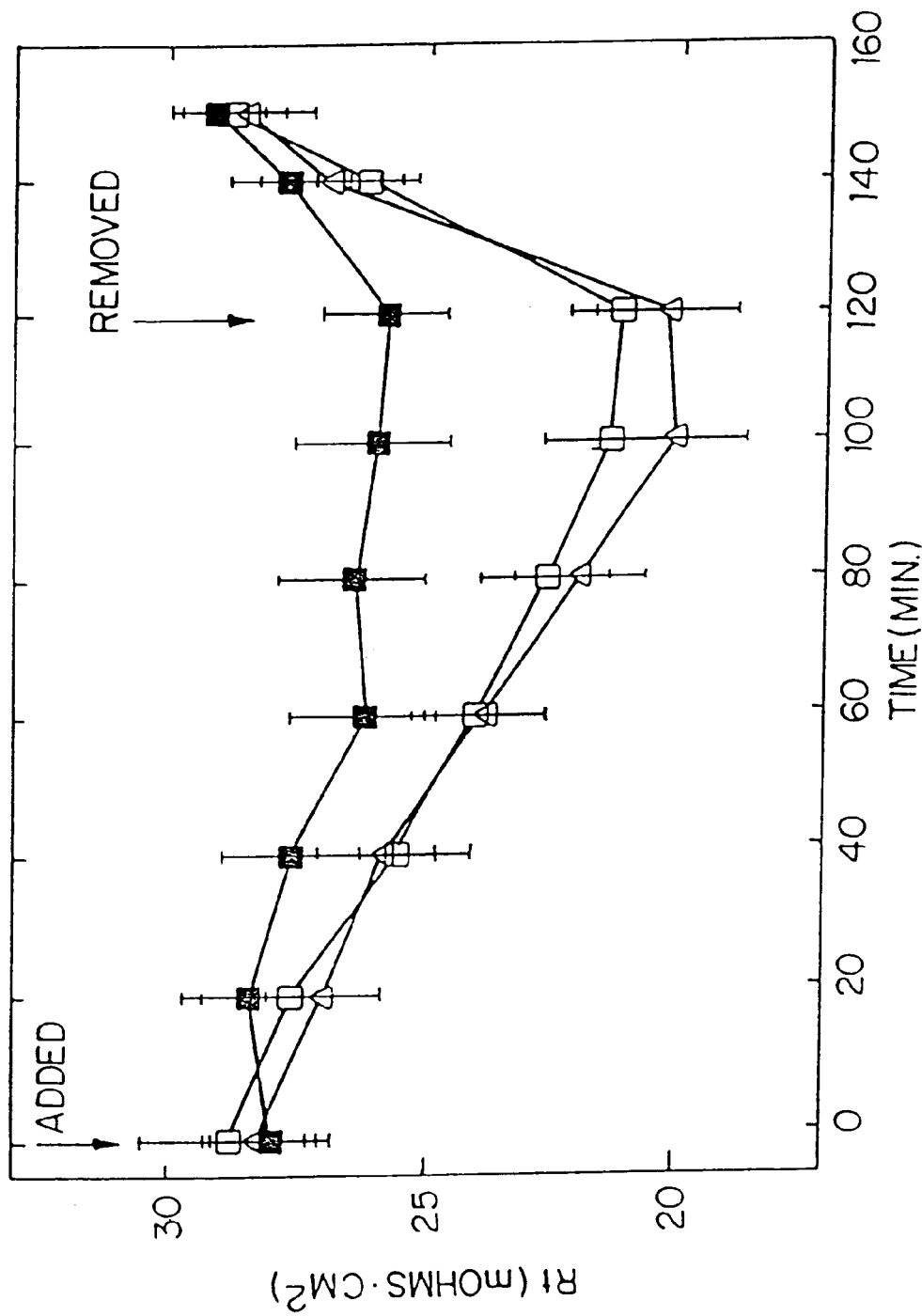

As shown in FIG. 4, purified MBP-ZOT fusion protein (Δ) was found to induce a Rt decrease in rabbit ileum comparable to that induced by purified ZOT (□), but significantly different when compared to the changes induced by the MBP negative control (■). Both purified MBP-ZOT and ZOT effects on Rt were readily reversible 24 hr following withdrawal of the moieties. These data demonstrate that the ZOT component of the MBP-ZOT fusion protein is still capable of recognizing and binding to the ZOT receptor.

In additional studies it has been found that ZOT exerts its permeabilizing effect only in the jejunum and ileum, while the colon remains unaffected. To define whether the regional effect of ZOT was related to the distribution of the ZOT receptor on the surface of the intestinal enterocytes, different intestinal segments, including jejunum, distal ileum, and colon, were fixed in 4.0% (v/v) paraformaldehyde, included, and cross-sectioned. The sections were then incubated for 30 min with either MBP-ZOT or MBP negative control. The samples were washed three times with PBS, blocked with 1.0% (w/v) bovine serum albumin, and then incubated for 1 hr with rabbit polyclonal anti-MBP antibodies (New England Biolabs) (dilution 1:500). The samples were then washed with PBS, and incubated with goat anti-rabbit IgG-FITC conjugated antibodies (Sigma) (dilution 1:100) for 30 min, followed by incubation with Evans blue (dilution 1:2000) for 10 min. The sections were finally analyzed with a fluorescence microscope (Optiphot: Nikon Inc., Melville, N.Y.).

The segments that showed a decrease in Rt, i.e., jejunum and distal ileum, displayed a significant number of fluorescent particles on the surface of the tissue, while no binding was observed in the same tracts of intestine exposed to the negative control. The fluorescent staining was maximal at the tip of the villi, and decreased along the villous axis. No significant staining was observed in the colonic segments exposed to ZOT (Fiore et al, *Gastroenterology*, 110:A323 (1996)).

These results demonstrate that the distribution of the ZOT receptor varies within the intestine, being more represented in the jejunum and distal ileum, and decreases along the villous-crypt axis. This distribution coincides with the regional effect of ZOT on Rt, and with the preferential F-actin redistribution induced by ZOT in the mature cells of the villi, suggesting that the regional distribution of ZOT receptor coincides with the different permeabilizing effect of ZOT on the various tracts of intestine tested. The paucity of ZOT receptors in the crypt area may reflect the fact that this region is already leaky as compared to the more mature epithelium of the tip of the villi (Marcial et al, *J. Membr. Biol.*, 80:59–70 (1984)), and thus does not need to be regulated.

The intestinal mucosa ultrastructural changes in adult humans affected by cholera has recently been reported (Mathan et al, *Gastroenterology*, 109:422–430 (1995)). Jejunal biopsies obtained during the acute phase of the disease showed a marked widening of the lateral intercellular spaces that was present only in the upper third of the villi, and was maximal at the villous tips, gradually decreasing towards the middle of the villus. A concomitant perijunctional actin condensation around the zonula adherens was also found. All of these morphological modifications were more abnormal in the humans with severe clinical illness, compared with the patients with moderate illness (Mathan et al, supra).

It is therefore believed in the present invention that the changes observed by Mathan et al, supra are associated to the preferential effect of ZOT on mature enterocytes of the villi, and thus, that the distribution of the ZOT receptor in humans is similar to that described in rabbits.

Binding experiments were also performed with several cell lines, including IEC6 cells, CaCo2, T84 (Nath et al, supra), MDCK, and bovine endothelial cells. More specifically, $2.0 \times 10^5$ of each of these cells were incubated at different time intervals (5 min, 30 min, 60 min), and temperatures (4° C. or 37° C.) with either $5 \times 10^{-9}$ M MBP-ZOT or $5.0 \times 10^{-9}$ M MBP negative control. The cells were then fixed with cold methanol, washed three times with PBS, blocked with 1.0% (w/v) bovine serum albumin, and then incubated for 1 hr with rabbit polyclonal anti-MBP antibodies (New England Biolabs) (dilution 1:500). The samples were then washed with PBS, and incubated with goat anti-rabbit IgG-FITC conjugated antibodies (Sigma) (dilution 1:100) for 30 min, followed by incubation with Evans blue (dilution 1:2000) for 10 min. The cells were finally analyzed with a fluorescence microscope (Optiphot: Nikon Inc., Melville, N.Y.).

When exposed to the MBP-ZOT fusion protein (at the various temperatures and time intervals tested) IEC6, CaCo2, and bovine endothelial cell monolayers, displayed a significant increased number of fluorescent particles, as compared to cells exposed to the MBP negative control. on the contrary, no significant staining was observed in T84 or MDCK cells when incubated with MBP-ZOT. These results suggest that ZOT interacts with a specific surface receptor whose distribution varies among different cell lines.

The same types of experiments were repeated using IEC6 monolayers exposed for 60 min at 4° C. to $10^{-10}$ M of the MBP-ZOT fusion protein, and then incubated with a 1:500 dilution of the anti-ZOT antiserum (obtained as described in Example 6 above). The monolayers were then washed with PBS, and incubated with goat anti-rabbit IgG-FITC conjugated antibodies (Sigma) (dilution 1:100) for 30 min, followed by incubation with Evans blue (dilution 1:2000) for 10 min. The cells were finally analyzed with a fluorescence microscope (Optiphot: Nikon Inc., Melville, N.Y.).

Again, cells exposed to the MBP-ZOT fusion protein (at the same time intervals and temperatures described above) showed a significant number of fluorescent particles, as compared to the MBP negative control. These results confirm that the ligand consisted of the MBP-ZOT fusion protein, and not a degradation product containing MBP, but not ZOT.

Similar results were obtained when using purified ZOT, and the same cell lines and experimental conditions tested above, and incubating the cell monolayers with anti-ZOT antiserum as described above.

To characterize the nature of the ZOT receptor, IEC6 cell monolayers were pre-treated with proteases (2.5 pg/ml protease K or 1.25 μg/ml pronase E) for 30 min at 37° C., and binding affinity for ZOT was determined as described above. In addition, 1.0 μg/ml of ZOT was pre-treated for 30 min hr at 37° C. with either 1.0 mM sucrose or 1.0 mM mannose, before applying ZOT onto the surface of the IEC6 monolayers. Binding affinity for ZOT was again determined as described above. It was found that binding of ZOT to the IEC6 cells was blocked by pre-treatment of the cell monolayers to either protease, and by pre-treatment of ZOT with sucrose, but not by pre-treatment with mannose (Fiore et al, supra). Based upon these results, it appears that the ZOT receptor is a glycoprotein.

B. ZOT Receptor Purification using MBP-ZOT

A MBP-ZOT affinity column was prepared by immobilizing overnight, at room temperature, 1.0 mg of purified MBP-ZOT (obtained as described in Example 5 above) to a pre-activated gel (Aminolink, Pierce). The column was washed with PBS, and then loaded with a crude cell lyzate obtained using either $10^6$ IEC6 cells (rat small intestinal cells) (Quaroni et al, *In: Methods in Cell Biology*, Chapter 20, 21B:403–426 (1980)); or CaCo2 cells (human intestinal cells) (Nath et al, *J. Diarrhoeal Dis.*, 8:133–142 (1990)). The lyzates were prepared by passing the cells through a 25 gauge needle three times. After a 90 min incubation at room temperature, the column was washed three times each with 14 ml of PBS, and the protein which bound to the MBP-ZOT-column was eluted from the column with 4.0 ml of a solution comprising 50 mM glycine (pH 2.5), 150 mM NaCl, and 0.1% (v/v) Triton X-100. The pH of the 1.0 ml eluted fractions was immediately neutralized with 1.0 N NaOH. The fractions were then subjected to 8.0% (w/v) SDS-PAGE under reducing conditions. SDS-PAGE was carried out as described by Davis, *Ann. N.Y. Acad. Sci.*, 121:404 (1964), and the gel stained with Comassie blue.

The eluted fractions from both the IEC6 and CaCo2 cell lysates loaded onto the MBP-ZOT affinity column, and subjected to SDS-PAGE, yielded a single protein band with a $M_r$ of 66 kDa, under reducing conditions. The single protein band from each cell line was then transferred to a nitrocellulose filter using CAPS buffer comprising 100 ml of (3-[cyclohexylamino]-1 propanesulfonic acid) 10×, 100 ml of methanol, 800 ml of distilled water. Then, the single protein band from each cell line was cut from the filter, and subjected to N-terminal sequencing as described by Hunkapiller, *In: Methods of Protein Microcharacterization*, Ed. Shibley, Chapters 11–12, Humana Press, pages 315–334 (1985), using a Perkin-Elmer Applied Biosystems Apparatus Model 494, and found to have the following N-terminal sequences: CaCo2 cells—Human ZOT receptor:

Xaa Leu His Lys Ser Glu Ala Ala His Arg Phe Lys Asp Leu Gln Glu (SEQ ID NO:10);

IEC6 cells—Rat ZOT receptor:

Ala His Lys Ser Glu Ile (SEQ ID NO:11).

A comparison of the N-terminal sequence of the resulting ZOT receptor from CaCo2 cells to the NBCI sequence database using BLAST revealed similarities to the N-terminal region of the human serum albumin (85% identity, 85% similarity) and to the N-terminal region of the human α-1-chimaerin (46% identity, 69% similarity) (see Table II below).

TABLE II

| | | | | | | | | | | | | | |
|---|---|---|---|---|---|---|---|---|---|---|---|---|---|
| CaCo2 ZOT receptor amino acids 2–14 | Leu | His | Lys | Ser | Glu | Ala | Ala | His | Arg | Phe | Lys | Asp | Leu (SEQ ID NO:12) |
| Human serum albumin amino acids 20–31 | Ala | His ○ | Lys ○ | Ser ○ | Glu ○ | Val | Ala ○ | His ○ | Arg ○ | Phe ○ | Lys ○ | Asp ○ | Leu ○ (SEQ ID NO:13) |
| α-1-chemaerin amino acids 17–29 | Val | His ○ | Lys ○ | Ser ○ | Lys + | Gln | Glu ○ | Gly | Arg | Gln + | Gln | Asp ○ | Leu ○ (SEQ ID NO:14) |
| Rat ZOT receptor amino acids 2–7 | Ala | His ○ | Lys ○ | Ser ○ | Glu ○ | Ile | (SEQ ID NO:11) | | | | | | |

○ indicates identity; + indicates similarity

α-1-chimaerin is a neuron-specific GTPase-activating protein for p21 rac, a member of the Ras-related rho subfamily (Dong, *Eur. J. Biochem.*, 227:636–646 (1994)). This small GTP-binding protein is involved in the regulation of actin filaments and cytoskeletal organization in mammalian cells in response to several stimuli (Ridley, *Cell*, 70:389–399 (1992)).

B. ZOT Receptor Purification using 6xHis-ZOT

A 6xHis-ZOT affinity column was prepared by immobilizing overnight, at room temperature, 1.0 mg of purified 6xHis-ZOT (obtained as described in Example 5 above) to a pre-activated gel (Aminolink, Pierce). The column was washed with PBS, and then loaded with a crude cell lyzate obtained using 15 g of tissue from human intestine, heart or brain. The lyzates were prepared by passing the tissue through a 25 gauge needle three times. After a 90 min incubation at room temperature, the column was washed three times each with 14 ml of PBS, and the protein which bound to the 6xHis-ZOT-column was eluted from the column with 4.0 ml of a solution comprising 50 mM glycine (pH 2.5), 150 mM NaCl, and 0.1% (v/v) Triton X-100. The pH of the 1.0 ml eluted fractions was immediately neutralized with 1.0 N NaOH. The fractions were then subjected to 8.0% (w/v) SDS-PAGE under reducing conditions. SDS-PAGE was carried out as described by Davis, *Ann. N.Y. Acad. Sci.*, 121:404 (1964), and the gel stained with Comassie blue.

The eluted fractions from the intestine, heart and brain tissues lysates loaded onto the 6xHis-ZOT affinity column, and subjected to SDS-PAGE, all yielded a single protein band with a $M_r$ of 45 kDa, under reducing conditions. The single protein band from each tissue was then transferred to a PVDF membrane (Biorad) using CAPS buffer comprising 100 ml of (3-[cyclohexylamino]-1 propanesulfonic acid) 10x, 100 ml of methanol, 800 ml of distilled water. Then, the single protein band from each tissue was cut from the filter, and subjected to N-terminal sequencing as described by Hunkapiller, *In: Methods of Protein Microcharacterization*, Ed. Shibley, Chapters 11–12, Humana Press, pages 315–334 (1985), using a Perkin-Elmer Applied Biosystems Apparatus Model 494, and found to have the following N-terminal sequences:

Human brain ZOT receptor:

Xaa Leu Thr Glu Leu Glu Lys Ala Leu Asn Xaa Gly Gly Gly Val Gly His Lys Tyr (SEQ ID NO:1);

Human intestine ZOT receptor:

Ser Ala Ile Phe Pro Ser Lys Xaa Ser Ala Ser Ile Gly (SEQ ID NO:2).

Human heart ZOT receptor:

Xaa Ala Gly Asn Lys Val Ile Ser Pro Ser Glu Asp Arg Arg Gln (SEQ ID NO:3)

A comparison of the N-terminal sequence of the resulting ZOT receptor from human brain to the NBCI sequence database using BLAST revealed similarities to the N-terminal region of Calprotectin (72% identity, 72% similarity) (see Table III below).

TABLE III

| | | | | | | | | | | | | | | | | | | | |
|---|---|---|---|---|---|---|---|---|---|---|---|---|---|---|---|---|---|---|---|
| Human Brain amino acids 2–19 (SEQ ID NO:15) | Leu | Thr | Glu | Leu | Glu | Lys | Ala | Leu | Asn | Xaa | Gly | Gly | Gly | Val | Gly | His | Lys | Tyr | |
| Calprotectin amino acids 2–19 (SEQ ID NO:16) | Leu ○ | Thr ○ | Glu ○ | Leu ○ | Glu ○ | Lys ○ | Ala ○ | Leu ○ | Asn ○ | Ser | Ile | Ile | Asp | Val ○ | Tyr | His ○ | Lys ○ | Tyr ○ | |

○ indicates identity; + indicates similarity

Calprotectin is a protein having a molecular weight of 8–14 kDa, and binds to calcium (Odink et al, *Nature*, 330:80–82 (1987); Lemarchand et al, *J. Biol. Chem.*, 267:19379–19382 (1992); and Schafer et al, *Biol. Chem. Hoppe Seyler*, 372:1–4 (1991)).

A comparison of the N-terminal sequence of the resulting ZOT receptor from human intestine to the NBCI sequence database using BLAST revealed similarities to an internal region of proteolipid protein (lipophilan) (92% identity, 92% similarity) (see Table IV below).

TABLE IV

| | | | | | | | | | | | | | |
|---|---|---|---|---|---|---|---|---|---|---|---|---|---|
| Human Intestine amino acids 1–13 | Ser | Ala | Ile | Phe | Pro | Ser | Lys | Xaa | Ser | Ala | Ser | Ile | Gly (SEQ ID NO:2) |
| Proteolipid Protein amino acids 186–198 | Ser ○ | Ala ○ | Ile ○ | Phe ○ | Pro ○ | Ser ○ | Lys ○ | Thr | Ser ○ | Ala ○ | Ser ○ | Ile ○ | Gly ○ (SEQ ID NO:17) |

○ indicates identity; + indicates similarity

Proteolipid protein (PLP) is a protein having a molecular weight of 30.5 kDa, and is an integral membrane protein that plays an important role in the formation or maintenance of the multi-lamellar structure of myelin (Diehl et al, *Proc. Natl. Acad. Sci., USA*, 83:9807–9811 (1986)).

A comparison of the N-terminal sequence of the resulting ZOT receptor from human heart to the NBCI sequence database using BLAST revealed similarities to the cardilipin-binding domain of creatine kinase (100% identity) (see Table V below).

Human creatine kinase sarcomeric mitochondrial protein is a protein having a molecular weight of 46 kDa, and places a central role in energy transduction in tissues with large, fluctuating energy demands.

While the invention has been described in detail, and with reference to specific embodiments thereof, it will be apparent to one of ordinary skill in the art that various changes and modifications can be made therein without departing from the spirit and scope thereof.

TABLE V

| | | | | | | | | | | | | | | |
|---|---|---|---|---|---|---|---|---|---|---|---|---|---|---|
| Human Heart amino acids 2–15 | Val | Arg | Glu | Gln | Pro | Arg | Leu | Phe | Pro | Pro | Ser | Ala | Asp | Tyr (SEQ ID NO:18) |
| Human Creatine Kinase, Sarcomeric Nitochondrial amino acids 41–54 | Val ○ | Arg ○ | Glu ○ | Gln ○ | Pro ○ | Arg ○ | Leu ○ | Phe ○ | Pro ○ | Pro ○ | Ser ○ | Ala ○ | Asp ○ | Tyr ○ |

○ indicates identity; + indicates similarity

What is claimed:

1. A method for screening for an antagonist of *Vibrio cholera* zonula occludens toxin (ZOT) comprising the steps of:

(A) carrying out an affinity binding assay on a test compound using purified *Vibrio cholera* zonula occludens toxin receptor having an apparent molecular weight of about 45 kDa, as determined by SDS-polyacrlyamide gel electrophoresis, wherein said receptor comprises at its N-terminal amino acid sequence, from positions 1 to 19, 1 to 13, or 1 to 15, the sequence of SEQ ID NO:1, SEQ ID NO:2, or SEQ ID NO:3, respectively, or a *Vibrio cholera* zonula occludens toxin receptor having an apparent molecular weight of about 66 kDa, as determined by SDS-polyacrlyamide gel electrophoresis, wherein said receptor comprises at its N-terminal amino acid sequence, from positions 1 to 16 of SEO ID NO:10, as the capture ligand; and (B) carrying out an assay on said test compound so as to determine whether said test compound possesses ZOT biological activity, wherein said ZOT biological activity is the ability to reversibly increase epithelial permeability by modulating the structure of intercellular tight junctions, wherein when said test compound specifically binds to said *Vibrio cholera* ZOT receptor, but does not possess ZOT biological activity, said test compound is determined to be an antagonist of *Vibrio cholera* ZOT.

2. A method for screening for an agonist of *Vibrio cholera* zonula occludens toxin (ZOT) comprising the steps of:

(A) carrying out an affinity binding assay on a test compound using purified *Vibrio cholera* zonula occludens toxin receptor having an apparent molecular weight of about 45 kDa, as determined by SDS-polyacrlyamide gel electrophoresis, wherein said receptor comprises at its N-terminal amino acid sequence, from positions 1 to 19, 1 to 13, or 1 to 15, the sequence of SEQ ID NO: 1, SEQ ID NO:2, or SEQ ID NO:3, respectively, or a *Vibrio cholera* zonula occludens toxin receptor having an apparent molecular weight of about 66 kDa, as determined by SDS-polyacrlyamide gel electrophoresis, wherein said receptor comprises at its N-terminal amino acid sequence, from positions 1 to 16 of SEQ ID NO:10, as the capture ligand; and (B) carrying out an assay on said test compound so as to determine whether said test compound possesses ZOT biological activity, wherein said ZOT biological activity is the ability to reversibly increase epithelial permeability by modulating the structure of intercellular tight junctions, wherein when said test compound specifically binds to said *Vibrio cholera* ZOT receptor, and possesses ZOT biological activity, said test compound is determined to be an agonist of *Vibrio cholera* ZOT.

* * * * *

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 19 amino acids
      (B) TYPE: amino acid
      (D) TOPOLOGY: linear (ii) MOLECULE TYPE: peptide (iii) HYPOTHETICAL: NO (xi) SEQUENCE DESCRIPTION: SEQ ID NO:1:

Xaa Leu Thr Glu Leu Glu Lys Ala Leu Asn Xaa Gly Gly Gly Val
   1            5                  10               15

Gly His Lys Tyr (2) INFORMATION FOR SEQ ID NO:2:

(i) SEQUENCE CHARACTERISTICS:
      (A) LENGTH: 13 amino acids
      (B) TYPE: amino acid
      (D) TOPOLOGY: linear (ii) MOLECULE TYPE: peptide (iii) HYPOTHETICAL: NO (xi) SEQUENCE DESCRIPTION: SEQ ID NO:2:

Ser Ala Ile Phe Pro Ser Lys Xaa Ser Ala Ser Ile Gly
   1            5                  10

(2) INFORMATION FOR SEQ ID NO:3:

(i) SEQUENCE CHARACTERISTICS:
      (A) LENGTH: 15 amino acids
      (B) TYPE: amino acid
      (D) TOPOLOGY: linear (ii) MOLECULE TYPE: peptide (iii) HYPOTHETICAL: NO (xi) SEQUENCE DESCRIPTION: SEQ ID NO:3:

Xaa Val Arg Glu Gln Pro Arg Leu Phe Pro Pro Ser Ala Asp Tyr
1               5                   10                  15

(2) INFORMATION FOR SEQ ID NO:4:

(i) SEQUENCE CHARACTERISTICS:
      (A) LENGTH: 14 amino acids
      (B) TYPE: amino acid
      (D) TOPOLOGY: linear (ii) MOLECULE TYPE: synthetic peptide (iii) HYPOTHETICAL: NO (xi) SEQUENCE DESCRIPTION: SEQ ID NO:4:

Ala Gly Asn Lys Val Ile Ser Pro Ser Glu Asp Arg Arg Gln
1               5                   10

(2) INFORMATION FOR SEQ ID NO:5:

(i) SEQUENCE CHARACTERISTICS:
      (A) LENGTH: 12 amino acids
      (B) TYPE: amino acid
      (D) TOPOLOGY: linear (ii) MOLECULE TYPE: synthetic peptide (iii) HYPOTHETICAL: NO (xi) SEQUENCE DESCRIPTION: SEQ ID NO:5:

Lys Gly Phe Ser Tyr Phe Gly Glu Asp Leu Met Pro
1               5                   10

(2) INFORMATION FOR SEQ ID NO:6:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:6:

CGGGATCCCG TATGAGTATC TTT					23

(2) INFORMATION FOR SEQ ID NO:7:

(i) SEQUENCE CHARACTERISTICS:
      (A) LENGTH: 24 nucleic acids
      (B) TYPE: nucleic acid
      (C) STRANDEDNESS: single
      (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:7:

CCCAAGCTTG GGTCAAAATA TACT					24

(2) INFORMATION FOR SEQ ID NO:8:

```
    (i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:8:

TCATCACGGC GCGCCAGG                                              18

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: synthetic DNA (iii) HYPOTHETICAL: NO (iv) ANTI-SENSE: NO (xi) SEQUENCE DESCRIPTION: SEQ ID NO:9:

GGAGGTCTAG AATCTGCCCG AT                                         22

(2) INFORMATION FOR SEQ ID NO:10:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:10:

Xaa Leu His Lys Ser Glu Ala Ala His Arg Phe Lys Asp Leu
    1               5                   10

Gln Glu
    15

(2) INFORMATION FOR SEQ ID NO:11:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:11:

Ala His Lys Ser Glu Ile
    1               5

(2) INFORMATION FOR SEQ ID NO:12:

(i) SEQUENCE CHARACTERISTICS:
        (A) LENGTH: 13 amino acids
        (B) TYPE: amino acid
        (D) TOPOLOGY: linear
```

(ii) MOLECULE TYPE: peptide (iii) HYPOTHETICAL: NO (xi) SEQUENCE DESCRIPTION: SEQ ID NO:12:

Leu His Lys Ser Glu Ala Ala His Arg Phe Lys Asp Leu
1               5                   10

(2) INFORMATION FOR SEQ ID NO:13:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:13:

Ala His Lys Ser Glu Val Ala His Arg Phe Lys Asp Leu
1               5                   10

(2) INFORMATION FOR SEQ ID NO:14:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:14:

Val His Lys Ser Lys Gln Glu Gly Arg Gln Gln Asp Leu
1               5                   10

(2) INFORMATION FOR SEQ ID NO:15:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:15:

Leu Thr Glu Leu Glu Lys Ala Leu Asn Xaa Gly Gly Gly Val
1               5                   10

Gly His Lys Tyr
15

(2) INFORMATION FOR SEQ ID NO:16:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:16:

Leu Thr Glu Leu Glu Lys Ala Leu Asn Ser Ile Ile Asp Val
1               5                   10

```
    Tyr His Lys Tyr
    15
```

(2) INFORMATION FOR SEQ ID NO:17:

```
    (i) SEQUENCE CHARACTERISTICS:
        (A) LENGTH: 13 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:17:

Ser Ala Ile Phe Pro Ser Lys Thr Ser Ala Ser Ile Gly
    1               5                   10
```

(2) INFORMATION FOR SEQ ID NO:18:

```
    (i) SEQUENCE CHARACTERISTICS:
        (A) LENGTH: 14 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:18:

Val Arg Glu Gln Pro Arg Leu Phe Pro Pro Ser Ala Asp Tyr
    1               5                   10
```